(12) United States Patent
Beaulieu et al.

(10) Patent No.: US 7,312,215 B2
(45) Date of Patent: Dec. 25, 2007

(54) BENZIMIDAZOLE C-2 HETEROCYCLES AS KINASE INHIBITORS

(75) Inventors: Francis Beaulieu, LaPrairie (CA); Anne Marinier, Kirkland (CA); Carl Ouellet, Boucherville (CA); Stephan Roy, St. Lambert (CA); Mark D. Wittman, Wallingford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 535 days.

(21) Appl. No.: 10/894,938

(22) Filed: Jul. 20, 2004

(65) Prior Publication Data

US 2005/0054655 A1    Mar. 10, 2005

Related U.S. Application Data

(60) Provisional application No. 60/490,889, filed on Jul. 29, 2003.

(51) Int. Cl.
*A61K 31/5377* (2006.01)
*C07D 413/14* (2006.01)

(52) U.S. Cl. .................. 514/234.5; 544/114; 544/122; 544/123; 544/131; 544/139

(58) Field of Classification Search ................ 544/114, 544/122, 123, 131, 139; 514/234.5
See application file for complete search history.

(56) References Cited

U.S. PATENT DOCUMENTS

| 5,650,415 | A | 7/1997 | Tang et al. |
| 6,465,484 | B1 | 10/2002 | Bilodeau et al. |

FOREIGN PATENT DOCUMENTS

| EP | 0 385 850 | 9/2000 |
| JP | 63-230687 | 9/1988 |
| WO | WO 99/60023 | 11/1999 |
| WO | WO 00/02871 | 1/2000 |
| WO | WO 00/08202 | 2/2000 |
| WO | WO 00/12089 | 3/2000 |
| WO | WO 00/17203 | 3/2000 |
| WO | WO 00/20023 | 4/2000 |
| WO | WO 00/23469 | 4/2000 |
| WO | WO 00/35455 | 6/2000 |
| WO | WO 00/53605 | 9/2000 |
| WO | WO 01/17995 | 3/2001 |
| WO | WO 01/60816 | 8/2001 |
| WO | WO 01/72751 | 10/2001 |
| WO | WO 02/079192 | 10/2002 |

OTHER PUBLICATIONS

Parrizas, et al. (1997) Endocrinology 138: 1427-1433.
Blum, et al. (2000) Biochemistry 39:15705-15712.
Gungor, et al. (1992) J. Med. Chem. 35:4455-4463.
Sahal, et al. (1988) Archives of Biochemistry and Biophysics 260:416-426.
U.S. Appl. No. 10/263,448, filed Oct. 2, 2002, Wittman et al.
U.S. Appl. No. 10/674,098, filed Sep. 29, 2003, Velaparthi et al.
Chimirri et al., Heterocycles, vol. 53, No. 3, pp. 613-620, 2000.
Nawwar et al., Chemical Abstract No. 164052r, vol. 120, No. 13, Mar. 28, 1994.
Pednekar et al., Chemical Abstracts No. 182731b, vol. 96, No. 22, May 31, 1982.

*Primary Examiner*—Rebecca Anderson
(74) *Attorney, Agent, or Firm*—Maureen S. Gibbons; Hong Liu

(57) ABSTRACT

Benzimidazole derivatives having the general formula I

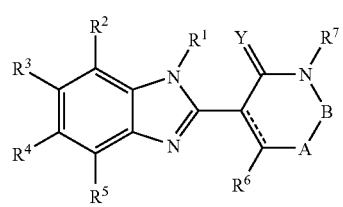

are provided. These compounds are useful as tyrosine kinase inhibitors, especially for the treatment of cancer.

8 Claims, No Drawings

BENZIMIDAZOLE C-2 HETEROCYCLES AS KINASE INHIBITORS

RELATED APPLICATIONS

This application claims priority benefit under Title 35 § 119(e) of U.S. Provisional Application No. 60/490,889, filed Jul. 29, 2003, the contents of which are herein incorporated by reference.

BACKGROUND

The present invention relates to compounds which inhibit tyrosine kinase enzymes, compositions which contain tyrosine kinase inhibiting compounds and methods of using inhibitors of tyrosine kinase enzymes to treat diseases which are characterized by an overexpression or upregulation of tyrosine kinase activity such as cancer, diabetes, restenosis, arteriosclerosis, psoriasis, angiogenic diseases and immunologic disorders (Powis, G.; Workman P. Signaling targets For The Development of Cancer Drugs. *Anti-Cancer Drug Design* (1994), 9: 263-277; Merenmies, J.; Parada, L. F.; Henkemeyer, M. Receptor Tyrosine Kinase Signaling in Vascular Development. *Cell Growth Differ* (1997) 8: 3-10; Shawver, L. K.; Lipsosn, K. E.; Fong, T. A. T.; McMahon, G.; Plowman, G. D.; Strawn, L. M. Receptor Tyrosine Kinases As Targets For Inhibition of Angiogenesis. *Drug Discovery Today* (1997) 2: 50-63; all herein incorporated by reference).

Tyrosine kinases play a critical role in signal transduction for several cellular functions including cell proliferation, carcinogenesis, apoptosis, and cell differentiation (Plowman, G. D.; Ullrich, A.; Shawver, L. K.: Receptor Tyrosine Kinases As Targets For Drug Intervention. *DN&P* (1994) 7: 334-339). Inhibitors of these enzymes are useful for the treatment or prevention of proliferative diseases which are dependent on these enzymes. Strong epidemiologic evidence suggests that the overexpression or activation of receptor protein tyrosine kinases leading to constitutive mitogenic signaling is an important factor in a growing number of human malignancies. Tyrosine kinases that have been implicated in these processes include Abl, CDK's, EGF, EMT, FGF, FAK, Flk-1/KDR, HER-2, IGF-1R, IR, LCK, MET, PDGF, Src, and VEGF (Traxler, P. M. Protein Tyrosine Kinase Inhibitors in Cancer Treatment. *Exp. Opin. Ther. Patents* (1997) 7: 571-588; Hence, there is an ongoing need to investigate novel compounds that can be used to regulate or inhibit tyrosine kinase enzymes.

SUMMARY OF THE INVENTION

The present invention is directed to compounds having Formula I that inhibit tyrosine kinase enzymes for the treatment of cancer:

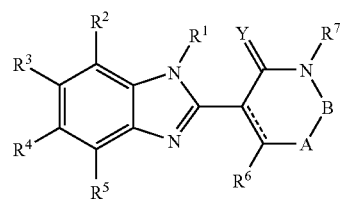

I

Y is O or S;
A is C=O, $C_1$-$C_3$ alkyl, $NR^7$ or a direct bond;
B is C=O or $NR^7$ provided that A and B are not both —$NR^7$;

$R^1$, $R^2$, $R^3$, $R^4$, $R^5$, $R^6$, and each $R^7$ are each independently selected from the group consisting of H, $C_{1-6}$ alkyl, alkenyl, alkynyl, cycloalkyl, heterocycloalkyl, halo, amino, aminoalkyl, alkoxy, thioalkoxy, nitro, aryl, heteroaryl, alkoxyalkyl, thioalkoxyalkyl, aminoalkyl, aralkyl, heteroarylalkyl, heterocycloalkylalkyl, —CN, —$CO_2R^8$, —$CONR^9R^{10}$, —$CO_2NR^{11}R^{12}$, —$NR^{13}CONR^{14}R^{15}$, —$NR^{16}SO_2R^{17}$, —$SO_2NR^{18}R^{19}$—$C(NR^{20})NR^{21}R^{22}$, —NH-Z, —NH-Z-aryl, and NH-Z-heteroaryl;

Z is selected from the group consisting of $C_1$-$C_4$ alkyl, alkenyl, and alkynyl; Z optionally having one or more hydroxy, thiol, alkoxy, thioalkoxy, amino, halo, $NR^{23}SO_2R^{24}$, —CO, —CNOH, —$CNOR^{26}$, —$CNNR^{27}$, —CNNCOR and —$CNNSO_2R^{29}$; and $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$ and $R^{26}$ are independently selected from the group consisting of H, alkyl, alkenyl, alkynyl, cycloalkyl, cycloalkylalkyl, hydroxy, alkoxy, aryl, heteroaryl, heterocyclyl, heteroarylalkyl, and alkyl-$R^{25}$ wherein $R^{25}$ is alkenyl, hydroxy, thiol, alkoxy, thioalkoxy, amino, alkylamino, dialkylamino, aryl, heteroaryl, cyano, halo, heteroaryl, heterocyloalkyl, sulfoxy, sulfonyl, —$NR^{27}COOR^{28}$, —$NR^{29}C(O)R^{30}$, —$NR^{31}SO_2R^{32}$, $SO_2NR^{31}R^{32}$—$C(O)NR^{33}R^{34}$, and $R^{27}$, $R^{28}$, $R^{28}R^{29}$, $R^{30}$, $R^{31}$, $R^{32}$ and $R^{34}$ are, independently, hydrogen, alkyl, or cycloalkyl.

Furthermore, the present invention is directed to methods for treating a condition associated with at least one tyrosine kinase inhibitor comprising administering to a mammal in need of such treatment a therapeutically effective amount of a compound of formula I and optionally at least one other anticancer agent.

The present invention also provides methods for treating cancer using the compounds of the present invention either alone or together with at least one other anticancer agent.

DETAILED DESCRIPTION

The term "alkyl" herein alone or as part of another group refers to a monovalent alkane (hydrocarbon) derived radical containing from 1 to 12 carbon atoms unless otherwise defined. An alkyl group is an optionally substituted straight, branched or cyclic saturated hydrocarbon group. When substituted, alkyl groups may be substituted with up to four substituent groups, at any available point of attachment. When the alkyl group is said to be substituted with an alkyl group, this is used interchangeably with "branched alkyl group". Exemplary alkyl groups include methyl, ethyl, propyl, isopropyl, n-butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, and the like. Exemplary substituents may include but are not limited to one or more of the following groups: hydroxy, halo (such as F, Cl, Br, I), haloalkyl (such as $CCl_3$ or $CF_3$), alkoxy, alkylthio, cyano, carboxy (—COOH), alkylcarbonyl (—C(O)R), alkoxycarbonyl (—OCOR), amino, carbamoyl (—NHCOOR or —OCONHR), urea (—NHCONHR), thiol, (—SH), sulfoxy, sulfonyl, aryl, heteroaryl, and heterocycloalkyl. Alkyl groups may also be represented by the formula alkyl-$R^{25}$. In preferred embodiments, the alkyl group is a methyl, ethyl, propyl or butyl group and includes substituted methyl, ethyl, propyl or butyl groups.

The term "alkenyl" herein alone or as part of another group refers to a hydrocarbon radical straight, branched or cyclic containing from 2 to 12 carbon atoms and at least one carbon to carbon double bond. An alkenyl group may be optionally substituted in the same manner as described for an alkyl group.

The term "alkynyl" herein alone or as part of another group refers to a hydrocarbon radical straight, branched or cyclic containing from 2 to 12 carbon atoms and at least one carbon to carbon triple bond. An alkynyl group may be optionally substituted in the same manner as described for an alkyl group.

The term "alkoxy" as used alone or in combination herein refers to a straight or branched chain alkyl group covalently bonded to the parent molecule through an oxygen atom linkage containing from one to ten carbon atoms and the terms "$C_{1-6}$ alkoxy" and "lower alkoxy" refer to such groups containing from one to six carbon atoms. Examples include, but are not limited to, methoxy, ethoxy, propoxy, isopropoxy, butoxy, t-butoxy and the like. The term "optionally substituted" when used in connection with an alkoxy substituent refers to the replacement of up to two hydrogens, preferably on different carbon atoms with a radical selected from the group of lower alkyl, phenyl, cyano, halo, trifluoromethyl, nitro, hydroxy, alkanoyl, amino, monoalkyl amino and dialkylamino. Alkoxy groups may be substituted in the same manner that alkyl groups can be substituted as described above.

The term "sulfoxy" herein alone or as part of a group refers to —SO and may be substituted with, for example, alkyl, aryl or heteroaryl groups.

The term "sulfonyl" herein alone or as part of a group refers to —SO$_2$ and may be substituted with alkyl, aryl or heteroaryl groups.

The term "amino" herein alone or as part of another group refers to —NH$_2$. An "amino" may optionally be substituted with one or two substituents, which may be the same or different, such as alkyl, aryl, arylalkyl, alkenyl, alkynyl, heteroaryl, heteroarylalkyl, cycloheteroalkyl, cycloheteroalkylalkyl, cycloalkyl, cycloalkylalkyl, haloalkyl, hydroxyalkyl, alkoxyalkyl or thioalkyl. Preferred substituents include alkylamino and dialkylamino, such as methylamino, ethylamino, dimethylamino, and diethylamino. These substituents may be further substituted with a carboxylic acid or any of the alkyl or aryl substituents set out herein. In addition, the amino substituents may be taken together with the nitrogen atom to which they are attached to form 1-pyrrolidinyl, 1-piperidinyl, 1-azepinyl, 4-morpholinyl, 4-thiamorpholinyl, 4-sulfoxymorpholine, 4-sulfonylmorpholine, 1-piperazinyl, 4-alkyl-1-piperazinyl, 4-arylalkyl-1-piperazinyl, 4-diarylalkyl-1-piperazinyl, 1-homopiperazinyl, 4-alkyl-1-homopiperazinyl, 4-arylalkyl-1-homopiperazinyl, 4-diarylalkyl-1-homopiperazinyl; 1-pyrrolidinyl, 1-piperidinyl, or 1-azepinyl, optionally substituted with alkyl, alkoxy, alkylthio, halo, trifluoromethyl or hydroxy.

The term "aryl" herein alone or as part of another group refers to monocyclic or bicyclic aromatic rings, e.g. phenyl, substituted phenyl and the like, as well as groups which are fused, e.g., napthyl, phenanthrenyl and the like. An aryl group thus contains at least one ring having at least 6 atoms, with up to five such rings being present, containing up to 22 atoms therein, with alternating (resonating) double bonds between adjacent carbon atoms or suitable heteroatoms. Aryl groups may optionally be substituted with one or more groups including, but not limited to halogen, alkyl, alkenyl, alkynyl, alkoxy, hydroxy, carboxy, carbamoyl, alkyloxycarbonyl, alkylaminocarbonyl, nitro, trifluoromethyl, amino, cycloalkyl, cyano, alkyl S(O)$_m$ (m=O, 1, 2), or thiol. Aryl groups may also be substituted with heterocycloalkyl and heterocycloaryl groups to form fused rings, such as dihydrobenzfuranyl, oxindolyl, indolyl, indolinyl, oxindolyl, benzoxazolidinonyl, benzoxazolinyl and benzoxazolidinone.

The term "cycloalkyl" herein alone or as part of another group refers to fully saturated and partially unsaturated hydrocarbon rings of 3 to 9, preferably 3 to 7 carbon atoms. Further, a cycloalkyl may be substituted. A substituted cycloalkyl refers to such rings having one, two, or three substituents, preferably one, selected from the group consisting of halo, alkyl, substituted alkyl, alkenyl, alkynyl, nitro, cyano, oxo (=O), hydroxy, alkoxy, thioalkyl, —CO$_2$R, —OC(=O)R, wherein R is H, alkyl, alkoxyalkyl, =N—OH, =N—O-alkyl, aryl, heteroaryl, heterocyclo, a five or six membered ketal (i.e. 1,3-dioxolane or 1,3-dioxane), —NR'R", —C(=O)NR'R", —OC(=O)NR'R", —NR'CO$_2$"R", —NRC(=O)R", —SO$_2$NR'R", and —NR'SO$_2$R", wherein each of R' and R" is independently selected from hydrogen, alkyl, substituted alkyl, and cycloalkyl, or R' and R" together form a heterocyclo or heteroaryl ring. Cycloalkyl groups may also be substituted with heteroatoms such as O, N, and S to form heterocycloalkyl groups. Preferred heterocycloalkyl groups include optionally substituted morpholine, homomorpholine (7 membered ring), thiomorpholine, piperazine, homopiperazine (7 membered ring), and piperidine, wherein the substituents are as defined above.

The term "heteroaryl" herein alone or as part of another group refers to substituted and unsubstituted aromatic 5 or 6 membered monocyclic groups, 9 or 10 membered bicyclic groups, and 11 to 14 membered tricyclic groups which have at least one heteroatom (O, S or N) in at least one of the rings. Each ring of the heteroaryl group containing a heteroatom can contain one or two oxygen or sulfur atoms and/or from one to four nitrogen atoms provided that the total number of heteroatoms in each ring is four or less and each ring has at least one carbon atom. The fused rings completing the bicyclic and tricyclic groups may contain only carbon atoms and may be saturated, partially saturated, or unsaturated. The nitrogen and sulfur atoms may optionally be oxidized and the nitrogen atoms may optionally be quaternized. Heteroaryl groups which are bicyclic or tricyclic must include at least one fully aromatic ring but the other fused ring or rings may be aromatic or non-aromatic. The heteroaryl group may be attached at any available nitrogen or carbon atom of any ring. The heteroaryl ring system may contain zero, one, two or three substituents selected from the group consisting of halo, alkyl, substituted alkyl, alkenyl, alkynyl, nitro, cyano, hydroxy, alkoxy, thioalkyl, —CO$_2$H, —OC(=O)H, —CO$_2$-alkyl, —OC(=O)alkyl, phenyl, benzyl, phenylethyl, phenyloxy, phenylthio, cycloalkyl, substituted cycloalkyl, heterocyclo, heteroaryl, —NR'R", —C(=O)NR'R", —OC(=O)NR'R", —NR'CO$_2$"R", —NR'C(=O)R", —SO$_2$NR'R", and —NR'SO$_2$R", wherein each of R' and R" is independently selected from hydrogen, alkyl, substituted alkyl, and cycloalkyl, or R' and R" together form a heterocyclo or heteroaryl ring.

Exemplary monocyclic heteroaryl groups include pyrfolyl, pyrrolidinyl, imidazolinyl, pyrazolyl, pyrazolinyl, imidazolyl, oxazolyl, isoxazolyl, thiazolyl, thiadiazolyl, isothiazolyl, furanyl, thienyl, oxadiazolyl, pyridyl, pyrazinyl, pyrimidinyl, pyridazinyl, triazinyl, and the like. Preferred heteroaryl groups include substituted imidazoles.

Exemplary bicyclic heteroaryl groups include indolyl, indolinyl, oxindolyl, benzoxazolidinone, benzothiazolyl, benzodioxolyl, benzoxazolyl, benzothienyl, quinolinyl, tetrahydroisoquinolinyl, isoquinolinyl, benzimidazolyl, benzopyranyl, indolizinyl, benzofuranyl, chromonyl, coumarinyl, benzopyranyl, cinnolinyl, quinoxalinyl, indazolyl, pyrrolopyridyl, furopyridinyl, dihydroisoindolyl, tetrahydroquinolinyl and the like.

Exemplary tricyclic heteroaryl groups include carbazolyl, benzindolyl, phenanthrollinyl, acridinyl, phenanthridinyl, xanthenyl and the like.

The term "halogen" or "halo" herein alone or as part of another group refers to chlorine, bromine, fluorine or iodine selected on an independent basis.

The term "hydroxy" herein alone or as part of another group refers to —OH.

The term "thioalkoxy" herein alone or as part of another group refers to an alkyl group as defined herein attached to the parent molecular group through a sulfur atom. Examples of thioalkoxy include, but are not limited to, thiomethoxy, thioethoxy, and the like.

Abbreviations: "Ph" represents phenyl; "Me" represents methyl; and "Et" represents ethyl.

The phrase "therapeutically effective amount" is intended to mean the amount of active compound or pharmaceutical agent that elicits the biological or medicinal response in a tissue, system, animal or human that is being sought by a researcher, veterinarian, medial doctor or other clinician.

An "anti-cancer agent" as used herein includes known anti-cancer treatments such as radiation therapy or with cytostatic or cytotoxic agents, such as for example, but not limited to, DNA interactive agents, such as cisplatin or doxorubicin; topoisomerase II inhibitors, such as etoposide; topoisomerase I inhibitors such as irinotecan or topotecan; tubulin interacting agents, such as paclitaxel, docetaxel or the epothilones; hormonal agents, such as tamoxifen; thymidilate synthase inhibitors, such as 5-fluorouracil; UFT alone or in combination with leucovorin; anti-metabolites, such as methotrexate; tyrosine kinase inhibitors such as Iressa and Tarceva; angiogenesis inhibitors; EGF inhibitors; Eg5 inhibitors; VEGF inhibitors; CDK inhibitors; Her1/2 inhibitors and monoclonal antibodies directed against growth factor receptors such as erbitux (EGF), herceptin (Her2), or avastin (VEGF).

When a functional group is termed "protected", this means that the group is in modified form to preclude undesired side reactions at the protected site. Suitable protecting groups for the compounds of the present invention will be recognized from the present application taking into account the level of skill in the art, and with reference to standard textbooks, such as Greene, T. W. et al., *Protective Groups in Organic Synthesis*, Wiley, N.Y. (1991).

When $C_{1-6}$ alkyl, alkenyl, alkynyl, cycloalkyl are substituted, they are preferably substituted with one or more hydroxy, cyano, carbamoyl, hydroxy, alkoxy, thiol, alkenyl, thioalkoxy, amino, alkylamino, amido, sulfonyl, sulfoxy, sulfonamido, halo, heterocycloalkyl, aryl or heteroaryl.

When aryl or heteroaryl are substituted, they are preferably substituted with one or more alkyl, alkenyl, alkynyl, cyano, carbamoyl, hydroxy, alkoxy, thioalkoxy, amino, amido, sulfonamido, halo or with R', R" wherein R', R" form a ring that is fused to the aryl group. When $CH_2$ aryl or heteroaryl are substituted, they are preferably substituted with one or more alkyl, alkenyl, alkynyl, cyano, carbamoyl, hydroxy, alkoxy, thioalkoxy, amino, amido, sulfonamido, or halogen.

When NH-Z-aryl or NH-Z-heteroaryl groups are substituted, they are preferably substituted with one or more alkyl, alkenyl, alkynyl, hydroxy, alkoxy, thioalkoxy, amino, halogen, nitro, nitrile, carboxylate, alkoxycarbonyl, carbamoyl, ester, amide, aryl, or heteroaryl groups.

The numbers in the subscript after the symbol "C" define the number of carbon atoms a particular group can contain. For example "$C_{1-6}$ alkyl" means a straight or branched saturated carbon chain having from one to six carbon atoms; examples include methyl, ethyl, n-propyl, isopropyl, n-butyl, sec-butyl, isobutyl, t-butyl, n-pentyl, sec-pentyl, isopentyl, and n-hexyl. Depending on the context, "$C_{1-6}$ alkyl" can also refer to $C_{1-6}$ alkylene which bridges two groups; examples include propane-1,3-diyl, butane-1,4-diyl, 2-methyl-butane-1,4-diyl, etc. "$C_{2-6}$ alkenyl" means a straight or branched carbon chain having at least one carbon-carbon double bond, and having from two to six carbon atoms; examples include ethenyl, propenyl, isopropenyl, butenyl, isobutenyl, pentenyl, and hexenyl. Depending on the context, "$C_{2-6}$ alkenyl" can also refer to $C_{2-6}$ alkenediyl which bridges two groups; examples include ethylene-1,2-diyl (vinylene), 2-methyl-2-butene-1,4-diyl, 2-hexene-1,6-diyl, etc. "$C_{2-6}$ alkynyl" means a straight or branched carbon chain having at least one carbon-carbon triple bond, and from two to six carbon atoms; examples include ethynyl, propynyl, butynyl, and hexynyl.

The term "alkyl-$R^{25}$" includes optionally substituted alkyl groups such as methyl, ethyl, propyl, and butyl, attached to an $R^{25}$ group. $R^{25}$ generally includes hydrogen, alkenyl, hydroxy, thiol, alkoxy, thioalkoxy, amino, alkylamino, dialkylamino, aryl, heteroaryl, cyano, halo, sulfoxy, sulfonyl, —NHCOOH, —NHC(O)—, —NHSO$_2$—, —C(O)NH$_2$, heteroaryl or heterocycloalkyl groups such as morpholinyl or a group having the formula:

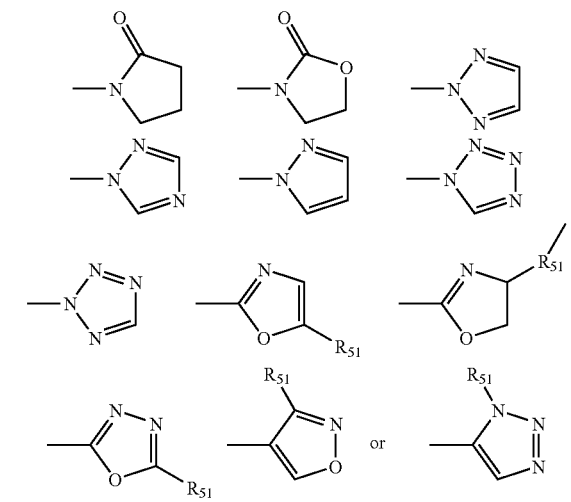

wherein $R_{51}$, is H or alkyl.

The terms "imidazole" and "imidazoline" herein alone or as part of another group includes substituted imidazoles and substituted imidazolines. Similarly, the term "tetrahydropyrimidine" includes substituted tetrahydropyrimidines. Likewise, the terms "piperazine", "piperidine" "morpholines", "homopiperazines", "homomorpholines" and "pyrrolidine" include substituted piperazines, substituted piperidines, substituted morpholines, substituted homomorpholines and substituted pyrrolidines, respectively.

The compounds of the present invention have the formula I

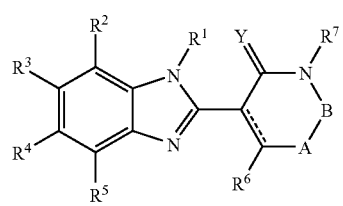

I and include pharmaceutically acceptable salts thereof, wherein

Y is O or S;

A is C=O, $C_1$-$C_3$ alkyl, $NR^7$ or a direct bond;

B is C=O or $NR^7$ provided that A and B are not both —$NR^7$;

$R^1$, $R^2$, $R^3$, $R^4$, $R^5$, $R^6$, and $R^7$ are each independently selected from the group consisting of H, $C_{1-6}$ alkyl, alkenyl, alkynyl, cycloalkyl, heterocycloalkyl, halo, amino, aminoalkyl, alkoxy, thioalkoxy, nitro, aryl, heteroaryl, alkoxyalkyl, thioalkoxyalkyl, aminoalkyl, aralkyl, heteroarylalkyl, heterocycloalkylalkyl, —CN, —$CO_2R^8$, —$CONR^9R^{10}$, —$CO_2NR^{11}R^{12}$, —$NR^{13}CONR^{14}R^{15}$, —$NR^{16}SO_2R^{17}$, —$SO_2NR^{18}R^{19}$, —$C(NR^{20})NR^{21}R^{22}$, —NH-Z, —NH-Z-aryl, and NH-Z-heteroaryl;

Z is selected from the group consisting of $C_1$-$C_4$ alkyl, alkenyl, and alkynyl; Z optionally having one or more hydroxy, thiol, alkoxy, thioalkoxy, amino, halo, $NR^{23}SO_2R^{24}$, —CO, —CNOH, —$CNOR^{26}$, —$CNNR^{27}$, —$CNNCOR^{28}$ and —$CNNSO_2R^{29}$; and $R^8$, $R^9$, $R^{10}$, $R^{11}$, $R^{12}$, $R^{13}$, $R^{14}$, $R^{15}$, $R^{16}$, $R^{17}$, $R^{18}$, $R^{19}$, $R^{20}$, $R^{21}$, $R^{22}$, $R^{23}$, $R^{24}$ and $R^{26}$ are independently selected from the group consisting of H, alkyl, alkenyl, alkynyl, cycloalkyl, cycloalkylalkyl, hydroxy, alkoxy, aryl, heteroaryl, heterocyclyl, heteroarylalkyl, and alkyl-$R^{25}$ wherein $R^{25}$ is alkenyl, hydroxy, thiol, alkoxy, thioalkoxy, amino, alkylamino, dialkylamino, aryl, heteroaryl, cyano, halo, heteroaryl, heterocyloalkyl, sulfoxy, sulfonyl, —$NR^{27}COOR^{28}$, —$NR^{29}C(O)R^{30}$, —$NR^{31}SO_2R^{32}SO_2NR^{31}R^{32}$—$C(O)NR^{33}R^{34}$, and $R^{27}$, $R^{28}$, $R^{29}$, $R^{30}$, $R^{31}$, $R^{32}$, $R^{33}$ and $R^{34}$ are, independently, hydrogen, alkyl, or cycloalkyl.

In preferred embodiments of the present invention A is C=O, CH, $CH_2$, $NR^7$ or a direct bond; B is C=O and $NR^7$; Y is O; $R^1$, $R^2$, $R^4$, $R^5$, and $R^7$ are each independently H or alkyl; $R^3$ is amino, aryl, heteroaryl, cycloalkyl or heterocycloalkyl; and $R^6$ is —NH-Z-aryl or —NH-Z-heteroaryl.

According to some embodiments, $R^3$ is a substituted or unsubstituted heterocycloalkyl, preferably a piperadine, morpholine, or a piperazine and may optionally be substituted with, for example a further heterocycloalkyl, preferably a 5 or 6 membered heterocycloalkyl.

The pharmaceutical compositions of the present invention containing the active ingredient may be in a form suitable for oral use, for example, as tablets, troches, lozenges, aqueous or oily suspensions, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of sweetening agents, flavoring agents, coloring agents and preserving agents in order to provide pharmaceutically elegant and palatable preparations. Tablets contain the active ingredient in admixture with non-toxic pharmaceutically acceptable excipients which are suitable for the manufacture of tablets. These excipients may be for example, inert diluents, such as calcium carbonate, sodium carbonate, lactose, calcium phosphate or sodium phosphate; granulating and disintegrating agents, for example, microcrystalline cellulose, sodium crosscarmellose, corn starch, or alginic acid; binding agents, for example starch, gelatin, polyvinylpyrrolidone or acacia, and lubricating agents, for example, magnesium stearate, stearic acid or talc. The tablets may be uncoated or they may be coated by known techniques to mask the unpleasant taste of the drug or delay disintegration and absorption in the gastrointestinal tract and thereby provide a sustained action over a longer period. For example, a water soluble taste masking material such as hydroxypropyl-methylcellulose or hydroxypropyl-cellulose, or a time delay material such as ethyl cellulose, cellulose acetate buryrate may be employed.

Formulations for oral use may also be presented as hard gelatin capsules wherein the active ingredient is mixed with an inert solid diluent, for example, calcium carbonate, calcium phosphate or kaolin, or as soft gelatin capsules wherein the active ingredient is mixed with water soluble carrier such as polyethyleneglycol or an oil medium, for example peanut oil, liquid paraffin, or olive oil.

Aqueous suspensions contain the active material in admixture with excipients suitable for the manufacture of aqueous suspensions. Such excipients are suspending agents, for example sodium carboxymethylcellulose, methylcellulose, hydroxypropylmethyl-cellulose, sodium alginate, polyvinyl-pyrrolidone, gum tragacanth and gum acacia; dispersing or wetting agents may be a naturally-occurring phosphatide, for example lecithin, or condensation products of an alkylene oxide with fatty acids, for example polyoxyethylene stearate, or condensation products of ethylene oxide with long chain aliphatic alcohols, for example heptadecaethylene-oxycetanol, or condensation products of ethylene oxide with partial esters derived from fatty acids and a hexitol such as polyoxyethylene sorbitol monooleate, or condensation products of ethylene oxide with partial esters derived from fatty acids and hexitol anhydrides, for example polyethylene sorbitan monooleate. The aqueous suspensions may also contain one or more preservatives, for example ethyl, or n-propyl p-hydroxybenzoate, one or more coloring agents, one or more flavoring agents, and one or more sweetening agents, such as sucrose, saccharin or aspartame.

Oily suspensions may be formulated by suspending the active ingredient in a vegetable oil, for example arachis oil, olive oil, sesame oil or coconut oil, or in mineral oil such as liquid paraffin. The oily suspensions may contain a thickening agent, for example beeswax, hard paraffin or cetyl alcohol. Sweetening agents such as those set forth above, and flavoring agents may be added to provide a palatable oral preparation. These compositions may be preserved by the addition of an anti-oxidant such as butylated hydroxyanisol or alpha-tocopherol.

Dispersible powders and granules suitable for preparation of an aqueous suspension by the addition of water provide the active ingredient in admixture with a dispersing or wetting agent, suspending agent and one or more preservatives. Suitable dispersing or wetting agents and suspending agents are exemplified by those already mentioned above. Additional excipients, for example sweetening, flavoring and coloring agents, may also be present. These compositions may be preserved by the addition of an anti-oxidant such as ascorbic acid.

The pharmaceutical compositions of the invention may also be in the form of an oil-in-water emulsions. The oily phase may be a vegetable oil, for example olive oil or arachis oil, or a mineral oil, for example liquid paraffin or mixtures of these. Suitable emulsifying agents may be naturally-occurring phosphatides, for example soy bean lecithin, and esters or partial esters derived from fatty acids and hexitol anhydrides, for example sorbitan monooleate, and condensation products of the said partial esters with ethylene oxide, for example polyoxyethylene sorbitan monooleate. The emulsions may also contain sweetening, flavoring agents, preservatives and antioxidants.

Syrups and elixirs may be formulated with sweetening agents, for example glycerol, propylene glycol, sorbitol or sucrose. Such formulations may also contain a demulcent, a preservative, flavoring and coloring agents and antioxidant.

The pharmaceutical compositions may be in the form of a sterile injectable aqueous solutions. Among the acceptable vehicles and solvents that may be employed are water, Ringer's solution and isotonic sodium chloride solution.

The sterile injectable preparation may also be a sterile injectable oil-in-water microemulsion where the active ingredient is dissolved in the oily phase. For example, the active ingredient may be first dissolved in a mixture of soybean oil and lecithin. The oil solution then introduced into a water and glycerol mixture and processed to form a microemulation.

The injectable solutions or microemulsions may be introduced into a patient's blood-stream by local bolus injection. Alternatively, it may be advantageous to administer the solution or microemulsion in such a way as to maintain a constant circulating concentration of the instant compound. In order to maintain such a constant concentration, a continuous intravenous delivery device may be utilized. An example of such a device is the Deltec CADD-PLUS.TM. model 5400 intravenous pump.

The pharmaceutical compositions may be in the form of a sterile injectable aqueous or oleagenous suspension for intramuscular and subcutaneous administration. This suspension may be formulated according to the known art using those suitable dispersing or wetting agents and suspending agents which have been mentioned above. The sterile injectable preparation may also be a sterile injectable solution or suspension in a non-toxic parenterally-acceptable diluent or solvent, for example as a solution in 1,3-butane diol. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectables.

Compounds of Formula I may also be administered in the form of a suppositories for rectal administration of the drug. These compositions can be prepared by mixing the drug with a suitable non-irritating excipient which is solid at ordinary temperatures but liquid at the rectal temperature and will therefore melt in the rectum to release the drug. Such materials include cocoa butter, glycerinated gelatin, hydrogenated vegetable oils, mixtures of polyethylene glycols of various molecular weights and fatty acid esters of polyethylene glycol.

For topical use, creams, ointments, jellies, solutions or suspensions, etc., containing the compound of Formula I are employed. (For purposes of this application, topical application shall include mouth washes and gargles.)

The compounds for the present invention can be administered in intranasal form via topical use of suitable intranasal vehicles and delivery devices, or via transdermal routes, using those forms of transdermal skin patches well known to those of ordinary skill in the art. To be administered in the form of a transdermal delivery system, the dosage administration will, of course, be continuous rather than intermittent throughout the dosage regimen. Compounds of the present invention may also be delivered as a suppository employing bases such as cocoa butter, glycerinated gelatin, hydrogenated vegetable oils, mixtures of polyethylene glycols of various molecular weights and fatty acid esters of polyethylene glycol.

When a compound according to this invention is administered into a human subject, the daily dosage will normally be determined by the prescribing physician with the dosage generally varying according to the age, weight, sex and response of the individual patient, as well as the severity of the patient's symptoms.

If formulated as a fixed dose, such combination products employ the compounds of this invention within the dosage range described above and the other pharmaceutically active agent or treatment within its approved dosage range. Compounds of formula I may also be administered sequentially with known anticancer or cytotoxic agents when a combination formulation is inappropriate. The invention is not limited in the sequence of administration; compounds of formula I may be administered either prior to or after administration of the known anticancer or cytotoxic agent(s).

Certain compounds of formula I may generally be prepared according to the following schemes and the knowledge of one skilled in the art. Solvates (e.g., hydrates of the compounds of formula I are also within the scope of the present invention. Methods of solvation are generally known in the art. Accordingly, the compounds of the instant invention may be in the free or hydrate form, and may be obtained by methods exemplified by the following schemes below.

More specifically, Schemes I-IX illustrate the preparation of compounds claimed in this invention. The examples, which follow, illustrate the compounds that can be synthesized by these schemes. The schemes are not limited by the examples listed or by any substituents employed for illustrative purposes.

Scheme I describes the preparation of the benzimidazoles. The starting diamines 1 are readily available using literature methods or are obtained commercially. The diamine is then condensed with an aldehyde 2 to provide the benzimidazole 3. Further modification of the functional groups on the aryl group of the benzimidazole or heterocycle of 3 is possible according to well-known organic methods.

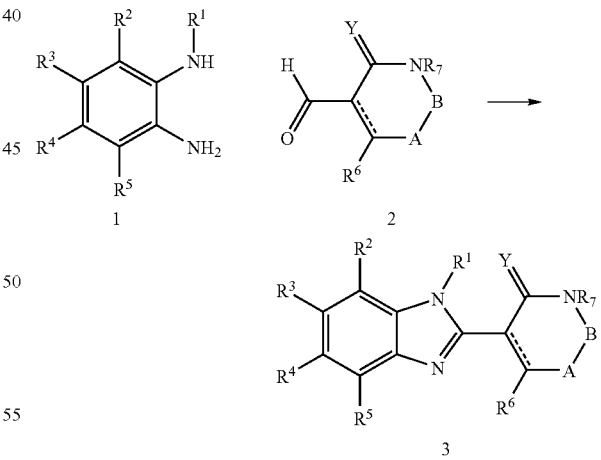

Alternatively, the benzimidazole could be formed in a step-wise manner (see Scheme II) by amide formation using the acid chloride of 5 or any of the commonly used peptide coupling reagents such as DCC (dicyclohexylcarbodiimide), EDCI (1-(3-dimethylaminopropyl)-3-ethylcarbodiimide hydrochloride), etc. Once the amide 6 is formed the nitro group is reduced using catalytic hydrogenation, transfer hydrogenation or a chemical reduction, using, for example, SnCl$_2$ or iron powder or other methods known in the art for reduction of aryl nitro groups. Treatment of the aniline with acid then forms the benzimidazole.

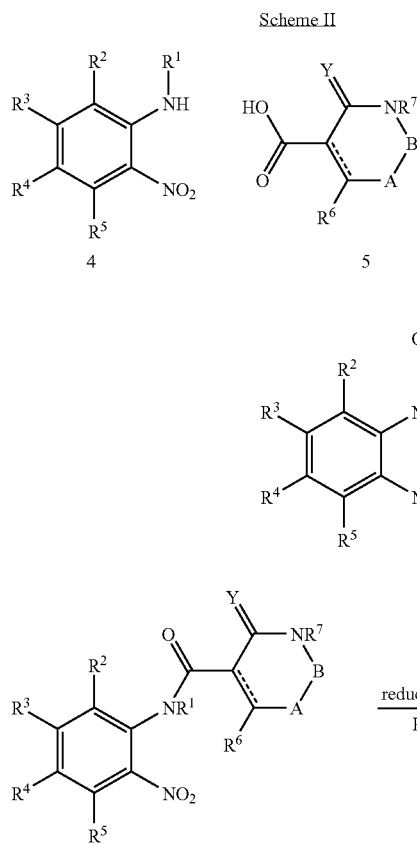

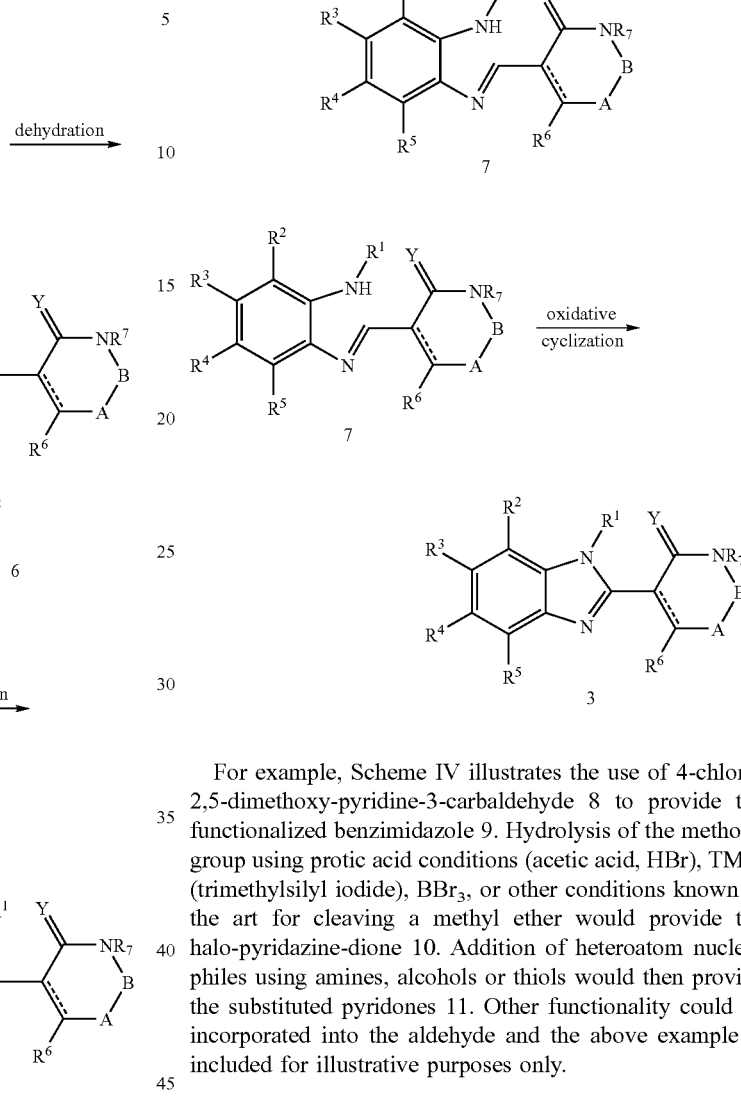

Scheme III illustrates a third method of benzimidazole formation in which the condensation of the diamine 1 with an aldehyde 2 provides the imine 7. Once the Schiff base 7 is formed the arylimine is induced to undergo oxidative cyclization using iodobenzene diacetate (IDB) as an oxidant to provide the benzimidazole 3.

For example, Scheme IV illustrates the use of 4-chloro-2,5-dimethoxy-pyridine-3-carbaldehyde 8 to provide the functionalized benzimidazole 9. Hydrolysis of the methoxy group using protic acid conditions (acetic acid, HBr), TMSI (trimethylsilyl iodide), BBr$_3$, or other conditions known in the art for cleaving a methyl ether would provide the halo-pyridazine-dione 10. Addition of heteroatom nucleophiles using amines, alcohols or thiols would then provide the substituted pyridones 11. Other functionality could be incorporated into the aldehyde and the above example is included for illustrative purposes only.

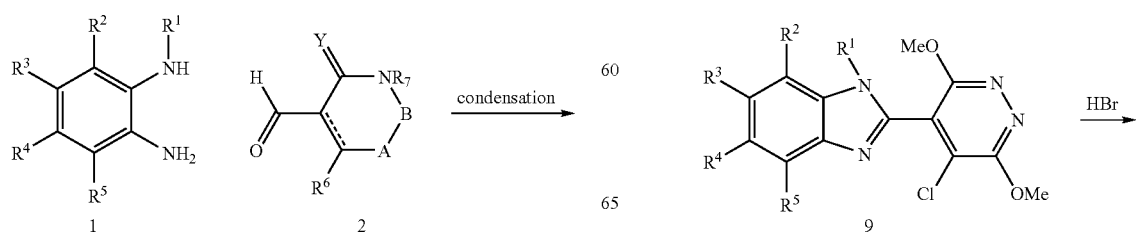

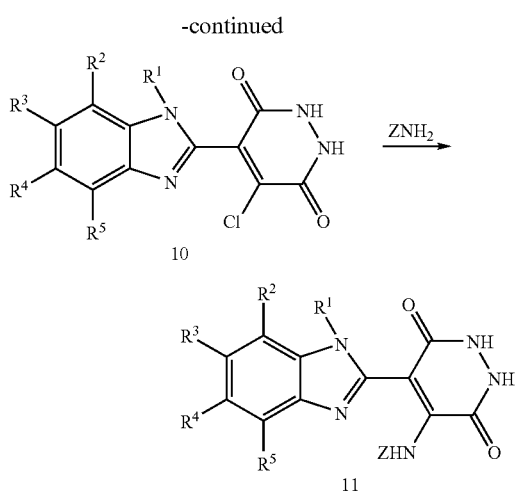

The aryl ring of the benzimidazole prepared using Schemes I-IV can be modified. For example introduction of a cyano group for $R^3$ on the benzimidazole allows for the formation of heterocycles at that position such as imidazole, imidazolines, oxazolines, thiazolines, amides, or amidines. Scheme V illustrates such transformations. Starting from the cyano-substituted benzimidazole 12 addition of an amine, alcohol or sulfide is possible according to known methods. Scheme V illustrates the addition of an amine ($NH_2Z$) to provide 13. Imidate formation preferably using ethanol and acid provides intermediate 14. Imidate 14 can be transformed using diamine to form imidazolines, amino alcohols to form oxazolines, amino acetals to form imidazoles, and amino thiols to form thiazolines 15. Alternatively the imidate can be hydrolyzed to the acid and coupled with amines using any of the standard amide formation reagents (DCC, EDCI, etc.) to form amides 16. Imidate 14 is also a useful intermediate for the preparation of amidines 17 by reacting with amines.

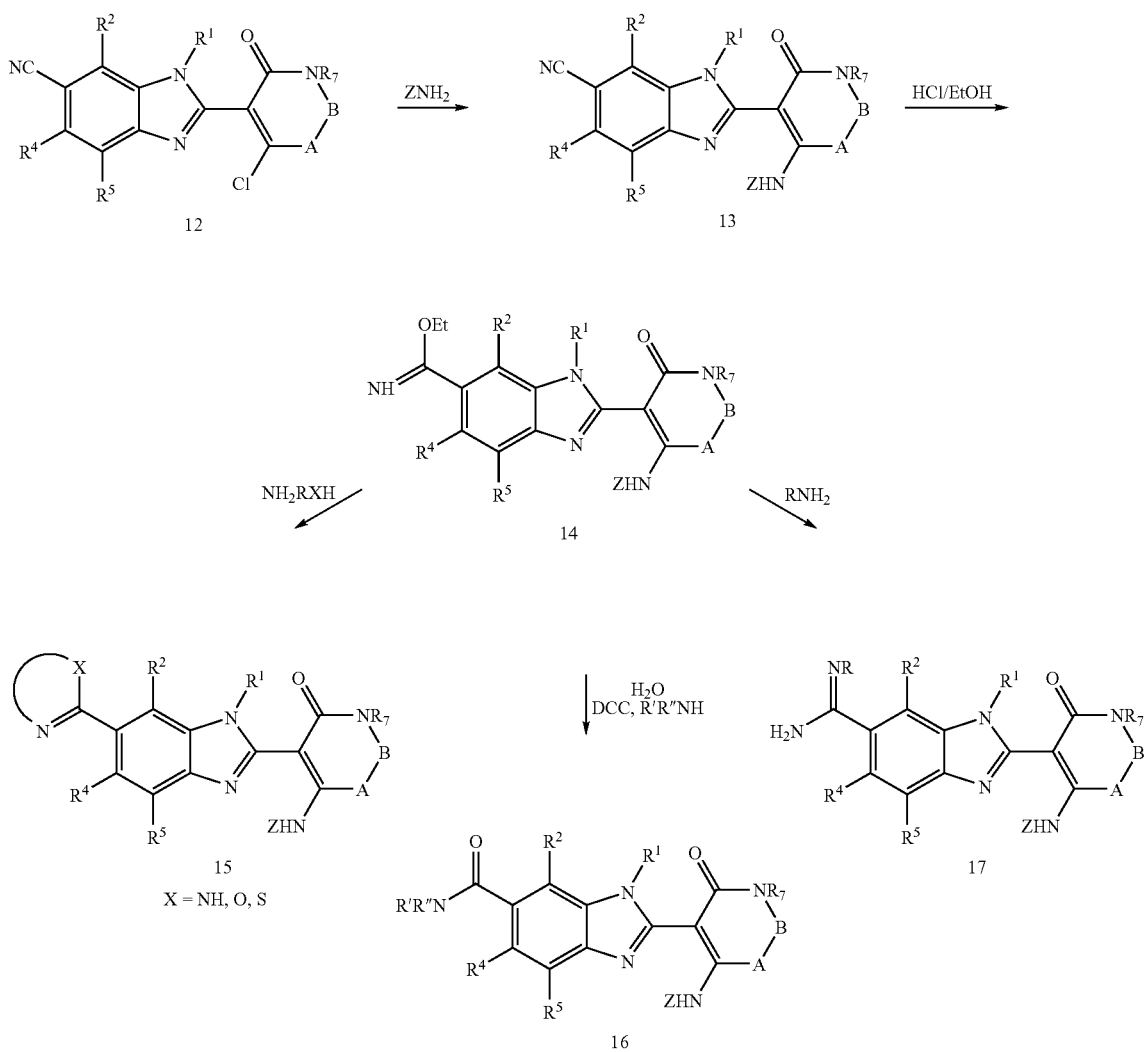

Scheme V

Scheme VI illustrates further transformation of benzimidazoles that bear a halogen atom using palladium catalysis using the general conditions developed by Suzuki [Yang et al. *Acta Chem. Scand.* (1993) 221; Suzuki et al. *Synth. Commun.* (1981) 11: 513] or Buchwald/Hartwig [Buchwald et al. *J. Am. Chem. Soc.* (1994) 116: 7901; Hartwig et al. *J. Am. Chem. Soc.* (1994) 116: 5969; Hartwig. *Angew. Chem., Int. Ed. Engl.* (1998) 37: 2046], herein incorporated by reference in their entirety. The preparation of a halogen substituted benzimidazole 18, preferably a bromide, can be done according to Schemes I, II or III, and can provide a substrate for Suzuki coupling with aryl, vinyl, and heterocyclic boronic acids to afford benzimidazoles 19. Amines and heterocycles such as piperazine or morpholine derivatives 20 can be prepared from the same halide, preferably a bromide, using amines under conditions generally described by Buchwald and Hartwig.

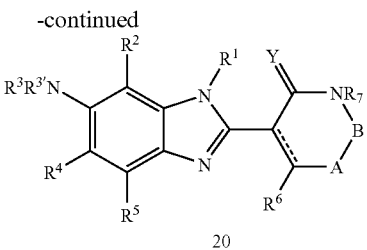

Alternatively amines, heterocycles, and alcohols can be introduced at $R_3$ using a nucleophilic aromatic substitution reaction started from an intermediate 21 where $R_3$ is halogen, preferably F, the halogen can be displaced with amines,

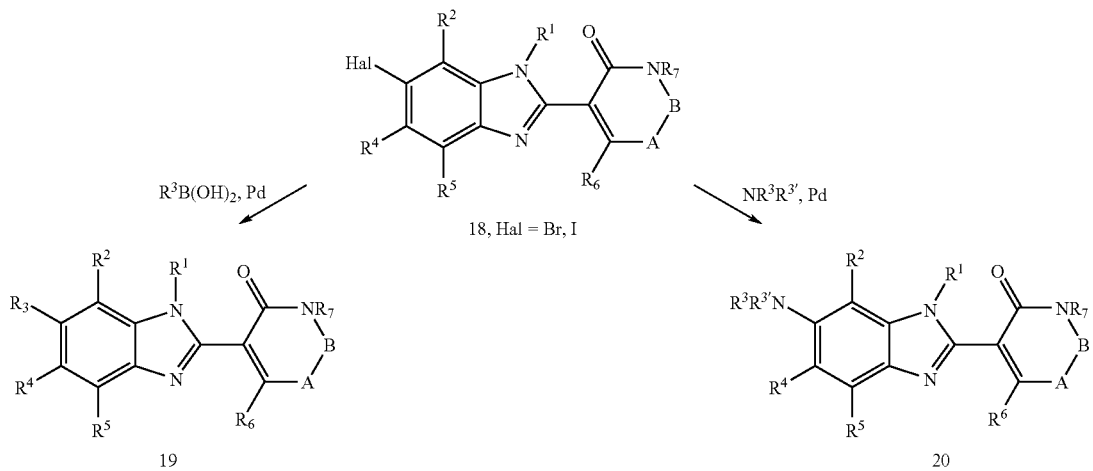

Alternatively amine and heterocyclic derivatives such as 20 can be prepared using intermediate 6 described in Scheme II. When the $R^3$ of 6 is a halogen, preferably F, the halogen can be displaced with amines, alcohols, heterocyclic amines and other nitrogen containing heterocycles such as piperazine, piperidine, 4-amino piperidine, morpholine, imidazole, etc. (Scheme VII). The terminal nitrogen of piperazine or 4-amino piperidine can then be alkylated using standard alkylation conditions or reacted with aldehydes in a reductive amination reaction to provide alkylated derivatives. Alternatively the terminal nitrogen atom of piperazine or 4-amino piperidine can be alkylated, acylated, or carbamoylated using any number of conditions that are routine for someone skilled in the art of organic synthesis.

alcohols, heterocyclic amines and other nitrogen containing heterocycles such as piperazine, piperidine, 4-amino piperidine, morpholine, imidazole, or substituted derivatives thereof (Scheme VIII). The terminal nitrogen of piperazine or 4-amino piperidine can then be alkylated using standard alkylation conditions or reacted with aldehydes in a reductive amination reaction to provide alkylated derivatives. Alternatively the terminal nitrogen atom of piperazine or 4-amino piperidine can be acylated or carbamoylated using any number of conditions that are routine for someone skilled in the art of organic synthesis. The resulting nitro aniline could be reduced to the diamine 22 and processed as illustrated in Scheme III.

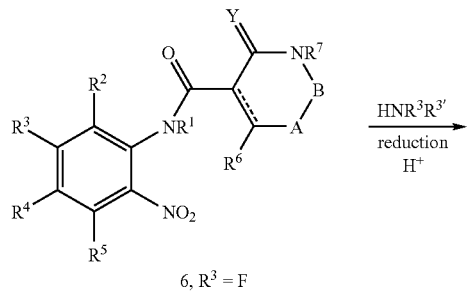

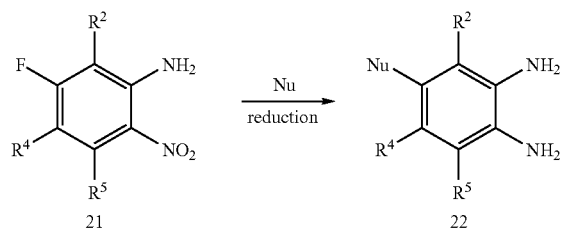

The preparation of suitably substituted pyridazines is illustrated in Scheme IX and exemplified by the synthesis of 4-chloro-2,5-dimethoxy-pyridine-3-carbaldehyde 8. Starting from the commercially available 2,5-dimethoxy pyridazine 23, metalation with a suitable lithium base, preferably Li-tetramethylpiperadine (LiTMP) at low temperature followed by trapping the anion with an electrophilic chlorinating agents such as NCS(N-chlorosuccinimide)or preferably Cl₃CCCl₃ would provide the 4-chloro derivative 24. A second metalation with a lithium base, preferably LiTMP and trapping with a formic acid derivative such as ethyl formate would provide 4-chloro-2,5-dimethoxy-pyridine-3-carbaldehyde 8, see, generally, [Pollet, P.; Turck, A.; Plé, N.; Quéguiner, G. *J. Org. Chem.*, (1999), 64, 4512; Plé, N.; Turck, A.; Couture, K.; Quéguiner, G. *Synthesis*, (1996), 838; Mattson, R. J.; Sloan, C. P. *J. Org. Chem.*, (1990), 55, 3410-3412], herein incorporated by reference in its entirety Scheme IX

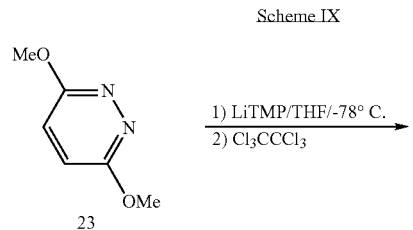

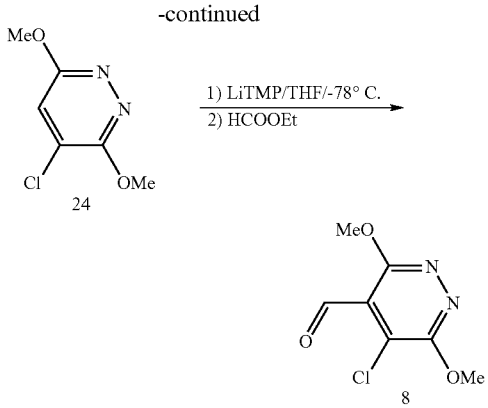

Scheme X describes the use of a specific aldehyde 25 following the general procedure outlined in Scheme I. The starting diamines 1 are readily available using literature methods or are obtained commercially. The diamine is then condensed with an aldehyde 25 to provide the benzimidazole 26. The chloro group of benzimidazole 26 can then be displaced with various nucleophiles such as amines, alcohols or sulfides. For illustration, an amine is used in Scheme X to provide compound 27. Acid hydrolysis of the methoxy groups of 27 would then provide the benzimidazole pyrimidinedione 28. Hydrolysis can be performed by various acids such as HCl, acetic acid or combinations thereof.

Scheme X

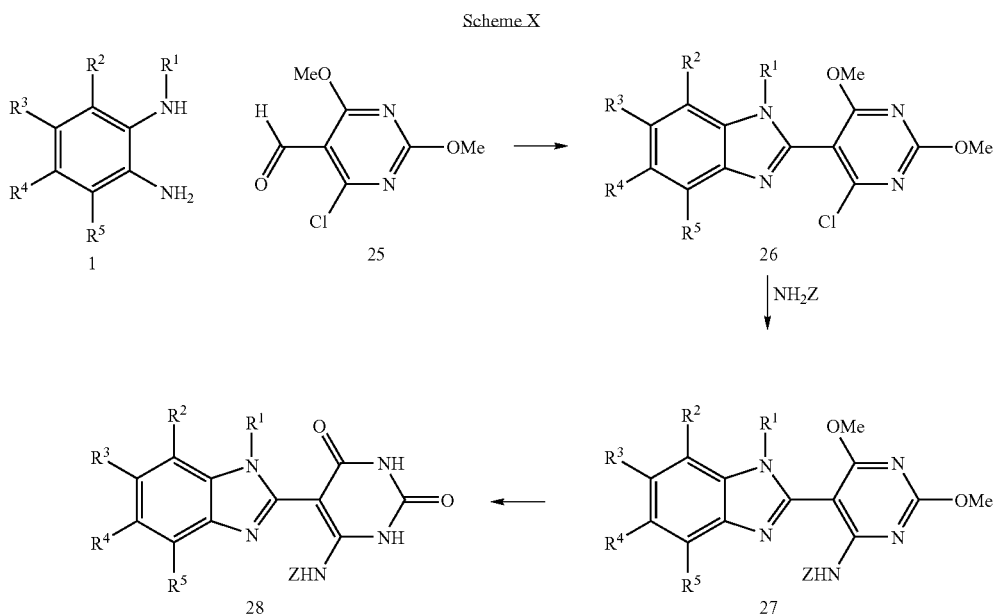

Aldehydes such as 25 are readily available from the substituted pyrimidines via metalation, as illustrated in Scheme XI. The substituted pyrimidine 29 can be metalated at low temperature using an alkyl lithium base and then formylated with a formic acid derivative such as ethyl formate.

Scheme XI

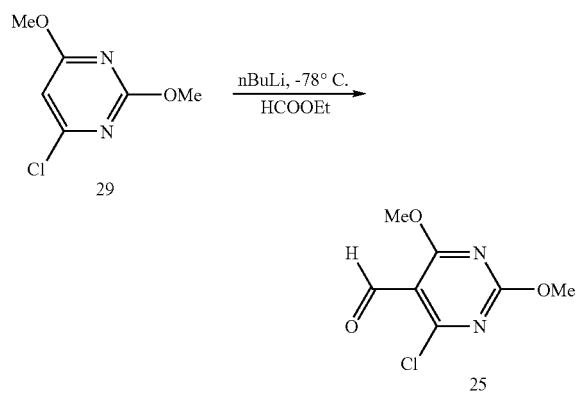

Scheme XII illustrates an alternative approach to compounds of Formula I. The same diamines 1 can be condensed with imidate 30 to give esters 31, which after treatment with a base such as sodium hydride, lithium bis(trimethylsilyl) amide or the like, may react with alkyl oxalyl, malonyl or succinyl halide and afford compounds 32. Subsequent treatment of these compounds with an alkylsulfonyl chloride such as methanesulfonyl or p-toluenesulfonyl chloride gives compounds 33 which can then be substituted with heteroatom nucleophiles such as amines, thiols or alcohols to provide compounds of type 34. Scheme XII illustrates the addition of an amine as the nucleophile. Cyclization with an amine gives the desired 5-, 6- or 7-membered cyclic cores 35.

Scheme XII

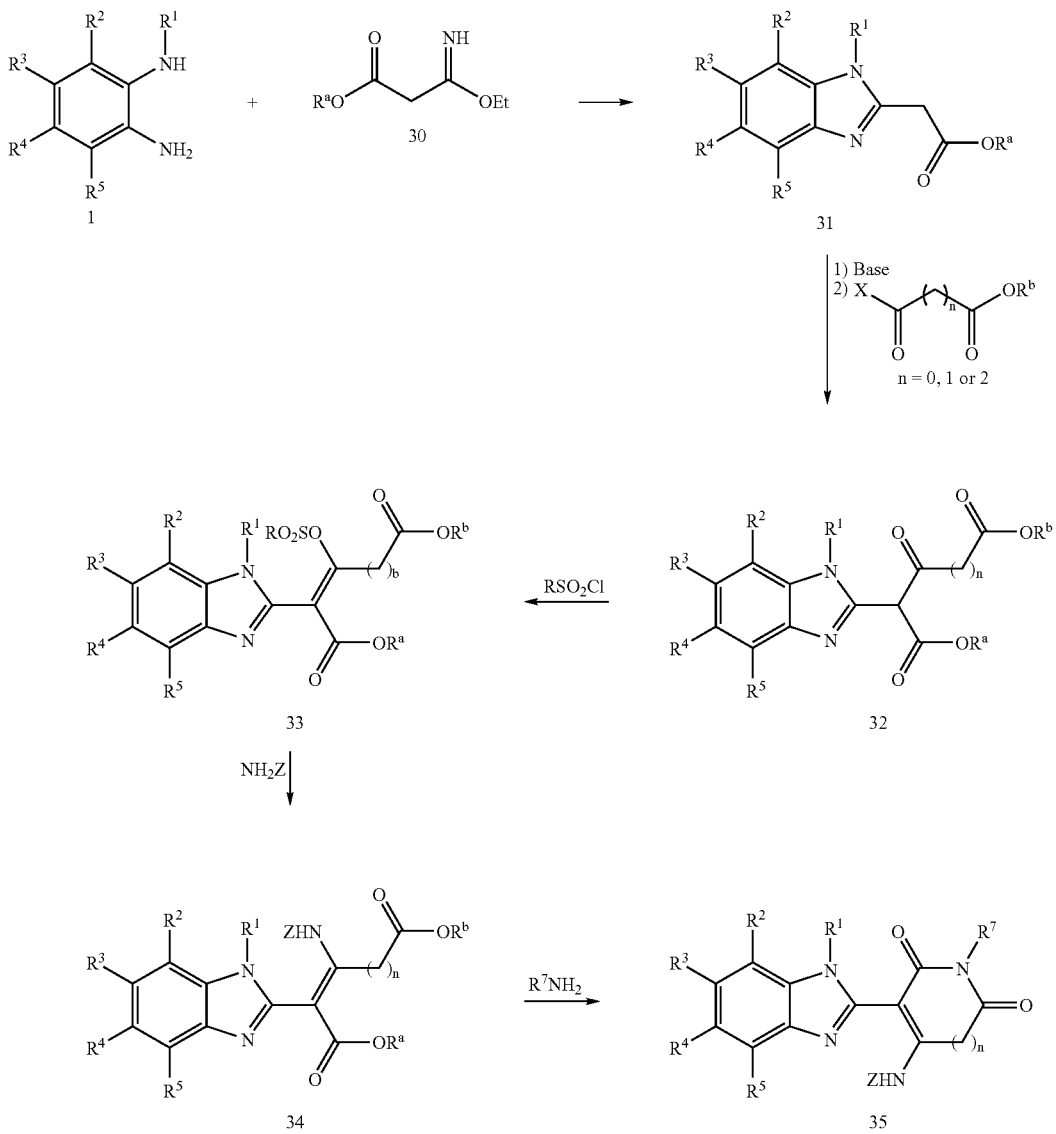

INTERMEDIATES AND EXAMPLES

General Procedure for the Preparation of 2-Hydroxy-2-(substituted-phenyl)-ethylamines:

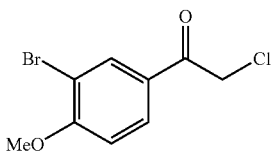

4-methoxy-3-bromophenyl chloroacetophenone: To a suspension of AlCl$_3$ (13.4 g, 0.10 mol) in methylene chloride (40 mL) was added a solution of 2-bromoanisole (12.5 mL, 0.10 mol) and chloroacetyl chloride (8 mL, 0.10 mol) at 0° C. The solution was warmed to ambient temperature for two hours and poured onto ice and extracted with methylene chloride, washed with saturated sodium bicarbonate solution, brine, and dried over MgSO$_4$. The solution was filtered, concentrated and crystalized from EtOH to give 15.37 g of white solid. LRMS [M−H]−260.8; IR (KBr) 1697, 1048, 1255 cm$^{-1}$; $^1$H NMR (300 MHz, CDCl$_3$) δ 8.18 (s, 1H), 7.94 (dd, J=8.67 Hz, 1H), 6.96 (d, J=8.67 Hz, 1H), 4.62 (s, 2H), 3.98 (s, 3H); $^3$C NMR (CDCl$_3$, 75.5 Hz) δ 188.8, 160.3, 134.1, 129.9, 128.2, 112.4, 111.3, 56.6, 45.3.

General Procedure for Chiral Reduction of Chloroketones and Ammonolysis:

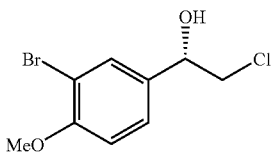

(S)-1-[4-methoxy-3-bromophenyl]-2-chloro ethanol: To a solution of (S)-Methyl-CBS-oxazaborolidine (1M in toluene, 0.745 mL, 0.745 mmol) and BH$_3$-THF (8 mL, 8 mmol) was added at the same time a solution BH$_3$-THF (19 mL, 19 mmol) and a solution of the chloroketone (10.03 g, 37.98 mmol) in 19 mL of THF. Both solutions were added dropwise over 30 minutes. The solution was stirred for 1 hour and quenched with the slow addition of methanol (50 mL). The solution was concentrated and the residue chromatographed over a short silica gel column (1:1 hexane/ethyl acetate) to give a quantitative yield (10.0 g) of chlorohydrin as a clear oil. IR (KBr) 1053, 1258, 3406 cm$^{-1}$; $^1$H NMR (300 MHz, CDCl$_3$) δ 7.59 (s, 1H), 7.30 (dd, J=2.16 Hz, 1H), 6.90 (d, J=8.46 Hz, 1H), 4.83 (dd, J=3.57 Hz, 1H), 3.90 (s, 3H), 3.64 (ddd, J=3.6, 11.1, 8.7, 2H), 2.04 (b s, 1H). $^3$C NMR (CDCl$_3$, 75.5 MHz) δ 155.9, 133.5, 131.1, 126.3, 111.9, 73.1, 60.4, 56.3, 50.7,

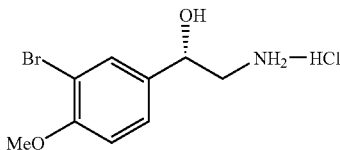

(S) 2-Amino-1-[3-chloro-4-methoxyphenyl]ethanol Hydrochloride: To a solution of the chlorohydrin (10.0 g, 37.9 mmol) in 120 mL of methanol at −40° C. was added 100 grams of ammonia. The solution was sealed in a pressure bottle and warmed to ambient temperature and stirred for 48 hours. The solution was cooled and opened. The ammonia was allowed to evaporate and solution concentrated. The residue was crystalized from ethanol/ethyl acetate to give 3.83 g of white solid (35%). The material was reacted with Boc$_2$O in ethyl acetate and saturated sodium bicarbonate and analyzed by chiral HPLC using a chiralcel OJ column using 95% hexane/ethanol as elutant and determined to by 98% ee. Additional crops were collected—2.96 g and 1.41 g for a total of 75% yield. LRMS [M+H]+246; IR (cm$^{-1}$, KBr) 1055, 1261, 3001, 2948, 3356; $^1$H NMR (500 MHz, DMSO) δ 8.09 (b s, 2H), 7.58 (s, 1H), 7.36 (dd, J=2.05, 6.45 Hz, 1H), 7.11 (d, J=8.5 Hz, 1H) 6.10 (s, 1H), 4.80 (m, 1H), 3.84 (s, 3H), 3.00 (ddd, J=2.7, 12.6, 9.5 Hz, 2H); $^{13}$C NMR (DMSO, 75.5 MHz) δ 154.8, 135.4, 130.4, 126.6, 112.4, 110.4, 67.9, 56.2, 45.4,

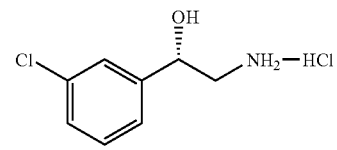

(S) 2-Amino-1-[3-chlorophenyl]ethanol Hydrochloride: was prepared according to the general procedure outlined above. LRMS [M+H]+172; IR (KBr, cm$^{-1}$) 3048, 3351, 2952; $^1$H NMR (300 MHz, MeOD) δ 7.48 (s, 1H), 7.35 (m, 3H), 3.31 (ddd, J=1.5, 3.12, 9.15 Hz 2H).

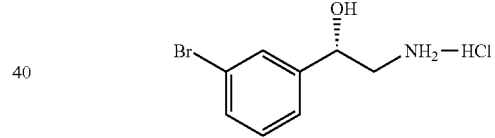

(S)-2-Amino-1-[3-bromophenyl]ethanol Hydrochloride: was prepared according to the general procedure outlined above. LRMS [MH]+217.9; IR (KBr, cm$^{-1}$) 3025, 3443, 2891; $^1$H NMR (500 MHz, DMSO) δ 7.93 (b s, 2H), 7.60 (s, 1H), 7.52 (d, 1H), 7.41 (s, 1H), 7.35 (d, J=7.7 Hz, 1H) 6.17 (s, 1H), 4.82 (m, 1H), 3.08 (ddd, J=2.6, 12.7, 9.6 Hz, 2H); $^{13}$C NMR (DMSO, 75.5 MHz) δ 144.4, 130.5, 128.7, 125.0, 121.6, 68.3, 45.1.

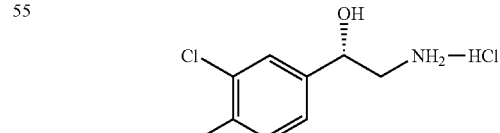

(S)-2-Amino-1-[3-chloro-4-methylthiophenyl]ethanol Hydrochloride: was prepared according to the general procedure outlined above. LRMS [M+H]+217.9; IR (KBr, cm$^{-1}$) 3007, 3358; $^1$H NMR (500 MHz, DMSO) δ 8.12 (b s, 2H), 7.46 (s, 1H), 7.37 (s, 1H), 7.35 (d, 1H) 6.19 (d, 1H), 4.83 (m, 1H), 3.01 (ddd, J=3.2, 12.8, 9.3 Hz, 2H); $^{13}$C NMR (DMSO, 75.5 MHz) δ 139.6, 136.5, 129.8, 126.6, 125.4, 68.0, 45.2, 14.2,

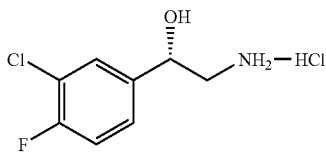

(S)-2-Amino-1-[3-chloro-4-fluoro-phenyl]ethanol Hydrochloride: was prepared according to the general procedure outlined above. LRMS [M+H]+189.9; IR (KBr, cm$^{-1}$) 1509, 3008, 3359; $^1$H NMR (500 MHz, DMSO) δ 8.21 (b s, 2H), 7.61 (d, J=7.85 Hz, 1H), 7.42 (m, 2H), 6.29 (s, 1H), 4.88 (m, 1H), 3.03 (ddd, J=3.4, 12.8, 9.2 Hz, 2H); $^{13}$C NMR (DMSO, 75.5 MHz) δ 157.5, 155.5, 139.7, 128.1, 126.7, 119.3, 116.7, 109.0, 67.8, 45.2,

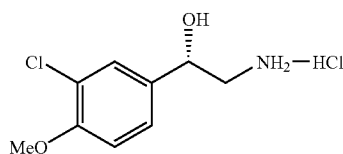

(S)-2-Amino-1-[3-chloro-4-methoxyphenyl]ethanol Hydrochloride: was prepared according to the general procedure outlined above. LRMS [M+H]+202; IR (KBr, cm$^{-1}$) 3354, 3003, 2949, 1288, 1064; $^1$H NMR (500 MHz, DMSO) δ 8.18 (brs, 3H), 7.43 (d, J=2.0 Hz, 1H), 7.31 (dd, J=8.5, 2.0 Hz, 1H), 7.14 (d, J=5.1 Hz, 1H), 6.11 (s, 1H), 4.81 (m, 1H), 3.84 (s, 3H), 2.99 (dd, J=13, 3.5 Hz, 1H), 2.83 (dd, J=12.5, 9 Hz, 1H); $^{13}$C NMR (DMSO, 125 MHz) δ 153.9, 135.0, 127.3, 125.8, 120.8, 112.6, 68.0, 56.1, 45.5; Elemental Analysis Calcd for C$_9$H$_{12}$ClNO$_2$—HCl: C, 45.39; H, 5.50; N, 5.88. Found: C, 45.38; H, 5.43; N, 5.70.

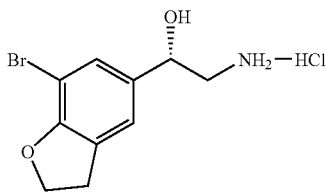

(S)-2-Amino-1-(7-bromo-2,3-dihydrobenzfuran-5-yl)-2-aminoethanol Hydrochloride: was prepared according to the general procedure outlined above.

LRMS [M+H]+258; IR (KBr, cm$^{-1}$) 3349, 3006, 2928, 1485, 1045, 983; $^1$H NMR (500 MHz, DMSO) δ 8.13 (brs, 3H), 7.29 (s, 1H), 7.23 (s, 1H), 6.08 (d, J=4 Hz, 1H), 4.76 (m, 1H), 4.61 (t, J=9 Hz, 2H), 3.29 (t, J=9 Hz, 2H), 2.96 (dd, J=13, 3.5 Hz, 1H), 2.82 (dd, J=13, 9.5 Hz, 1H); $^{13}$C NMR (DMSO, 125 MHz) δ 156.3, 135.9, 129.1, 128.1, 122.1, 100.9, 71.5, 68.2, 45.6, 29.9; E mental Analysis Calcd for C$_{10}$H$_{12}$BrNO$_2$—HCl: C, 40.77; H, 4.44; N, 4.75. Found: C, 40.77; H, 4.63; N, 4.63.

General Procedure for the Preparation of 2-Amino-3-(Substituted-phenyl)-propanol:

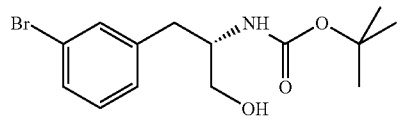

(S)-[2-(3-Bromo-phenyl)-1-hydroxymethyl-ethyl]-carbamic acid tert-butyl ester:

To a solution of (S)-3-(3-bromo-phenyl)-2-tert-butoxycarbonylamino-propinic acid (500 mg, 1.45 mmol) in THF (30 mL) was added borane-tetrahydrofuran complex (1.0 M solution) (4.35 mL, 4.35 mmol). The reaction mixture was stirred at room temperature for 14 h and quenched with acetic acid (1 mL). After removal of most solvent, the residue was extracted with EtOAc, washed with brine, dried over Na$_2$SO$_4$. After concentration, the crude product (400 mg, 83%) was used for the next step without purification. LCMS (M+H)$^+$ m/z 330 (t=1.61 min).

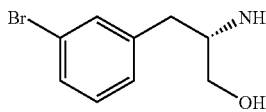

(S)-2-Amino-3-(3-bromo-phenyl)-propan-1-ol: To a solution of (S)-[2-(3-bromo-phenyl)-1-hydroxymethyl-ethyl]-carbamic acid tert-butyl ester (400 mg, 1.21 mmol) in methanol (30 mL) was added 4 M HCl in dioxane (2 mL, excess). The reaction mixture was stirred at room temperature for 14 h. After concentration in vacuo, the residue was used for the next step without purification. LCMS (M+H)$^+$ m/z 230 (t=0.78 min.)

Procedure for the Preparation of 5-imidazol-1-yl-3-methyl-benzene-1,2-diamine

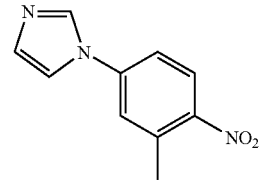

1-(3-Methyl-4-nitro-phenyl)-1H-imidazole: To a solution of 4-fluoro-2-methyl-1-nitro-benzene (300 mg, 1.84 mmol) in DMSO (2 mL) were added KOH (20 mg, 3.87 mmol) and imidazole (263 mg, 3.88 mmol). The reaction mixture was heated to 100° C. for 3.5 h, cooled to room temperature, and diluted with ice-cold water. The resulting precipitate was filtered, washed with ice-cold water, and dried under vacuum to give the title compound (310 mg, 80%) as a yellow powder. $^1$H NMR (300 MHz, DMSO-d$_6$) δ 8.46 (1H, s), 8.16 (1H, d, J=8.9 Hz), 7.90-7.92 (2H, m), 7.78 (1H, dd, J=2.5, 8.9 Hz), 7.17 (1H, s), 2.61 (3H, s). LRMS (M+H)$^+$mz 204.

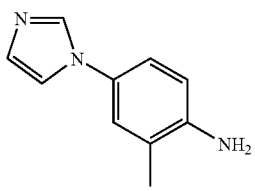

4-Imidazol-1-yl-2-methyl-phenylamine: To 1-(3-methyl-4-nitro-phenyl)-1H-imidazole (200 mg, 0.98 mmol) and 10% Palladium on carbon (35 mg) was added degassed methanol (3 mL). The suspension was flushed and evacuated with hydrogen/vacuum line. The suspension was allowed to stir at room temperature for 14 h under hydrogen atmosphere (hydrogen balloon). The dark reaction mixture was filtered through a pad of celite and rinsed with methanol. Concentration of the filtrate gave the title compound (166 mg, 98%) which was used for the next step without purification. $^1$H NMR (300 MHz, DMSO-d$_6$) δ 7.95 (1H, s), 7.48 (1H, s), 7.16 (1H, narrow d, J=2.5 Hz), 7.09 (1H, dd, J=2.5, 8.4 Hz), 7.01 (1H, s), 6.67 (1H, d, J=8.4 Hz), 5.03 (2H, broad s), 2,10 (3H, s).

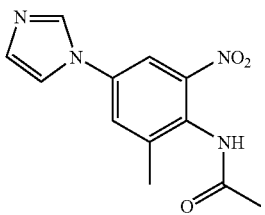

N-(4-Imidazol-1-yl-2-methyl-6-nitro-phenyl)-acetamide: To a solution of 4-imidazol-1-yl-2-methyl-phenylamine (1 g, 5.78 mmol) in CH$_2$Cl$_2$ (20 mL) was added Ac$_2$O (0.7 mL, 7.28 mmol) at 0° C. The reaction mixture was stirred at room temperature for 14 h and diluted with water. The aqueous layer was extracted with CH$_2$Cl$_2$ and the combined organic layers were washed with saturated NaHCO$_3$ and brine, dried over Na$_2$SO$_4$, and concentrated in vacuo to give a white solid. The white solid was suspended in H$_2$SO$_4$ (conc.) (15 μL). Then HNO$_3$ (conc.) (0.312 mL) was added to the suspension at 0° C. The reaction mixture was slowly warmed to room temperature and stirred at room temperature for 4 h. After cooling to −10° C., the reaction mixture was neutralized with ammonium hydroxide extracted with ethyl acetate. The combined organic layers were washed with brine, dried over Na$_2$SO$_4$, and concentrated. The residue was purified by flash chromatography (1:9:5 MeOH/THF/hexane) to yield the title compound (0.61 g, 41%). $^1$H NMR (300 MHz, CD$_3$OD) δ 8.11 (1H, s), 7.45-7.56 (2H, m), 7.38 (1H, dd, J=2.4, 8.4 Hz), 7.14 (1H, s), 2.33 (3H, s), 2.18 (3H, s).

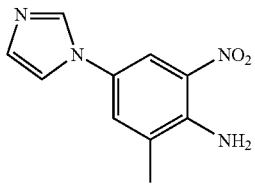

(4-Imidazol-1-yl-2-methyl-6-nitro-phenylamine: To a suspension of N-(4-imidazol-1-yl-2-methyl-6-nitro-phenyl)-acetamide (279 mg, 1.07 mmol) in ethanol (3 mL) was added 2 N HCl (2 mL). The reaction mixture was heated to reflux for 14 h, cooled to room temperature, and neutralized with saturated NaHCO$_3$. The resulting bright orange solid was filtered and dried under vacuum. The title compound (179 mg, 76%) was obtained as an orange solid. $^1$H NMR (300 MHz, CD$_3$OD) δ 8.78 (1H, s), 8.24 (1H, s), 7.78 (1H, s), 7.64 (1H, s), 7.46 (1H, s), 2.36 (3H, s).

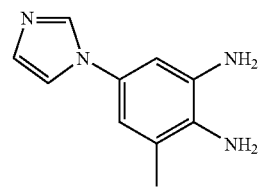

5-Imidazol-1-yl-3-methyl-benzene-1,2-diamine: To 4-imidazol-1-yl-2-methyl-6-nitro-phenylamine (350 mg, 1.61 mmol) and 10% Palladium on carbon (40 mg) were added degassed methanol (5 mL) and TFA (5 drops). The reaction mixture was flushed and evacuated with hydrogen/vacuum line, stirred at room temperature for 14 h under hydrogen atmosphere (hydrogen balloon). The dark reaction mixture was filtered through a pad of celite and rinsed with methanol. Concentration of the filtrate gave the residue, which was diluted with water, and extracted with ethyl acetate. The combined organic layers were washed with saturated NaHCO$_3$, and brine and dried over Na$_2$SO$_4$. Concentration to dryness gave the title compound (275 mg, 91%) as a solid. $^1$H NMR (300 MHz, CD$_3$OD) δ 7.87 (1H, s), 7.34 (1H, s), 7.05 (1H, s), 6.72 (1H, d, J=2.4 Hz), 6.65 (1H, d, J=2.4 Hz) 2.21 (3H, s). LCMS (M+H)$^+$ m/z 189 (t=0.23 min.).

Procedure for the Preparation of 3,4-diamino-5-methyl-benzonitrile

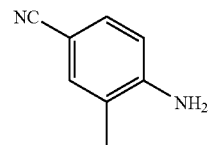

4-Amino-3-methyl-benzonitrile: To a solution of 3-methyl-4-nitro-benzonitrile (20 g, 0.123 mol) in HOAc (200 mL) was added iron powder (17.55 g, 0.309 mol). After 10 min, the reaction was exothermic and turned to dark color. The reaction mixture was allowed to stir at room temperature for 14 h and then diluted with EtOAc (200 mL). The brown precipitate was filtered through a pad of celite and the filtercake was rinsed with EtOAc. The filtrate was concentrated in vacuo and the residue was purified by flash chromatography (40% EtOAc/hexane) to yield the title compound (15.3 g, 92%). $^1$H NMR (300 MHz, CDCl$_3$) δ 7.30-7.34 (2H, m), 6.64 (1H, d, J=8.7 Hz), 2.16 (3H, s). LCMS (M+H)$^+$ m/z 133 (t=0.93 min).

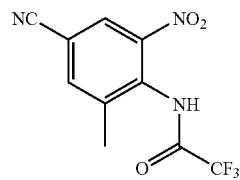

N-(4-Cyano-2-methyl-6-nitro-phenyl)-2,2,2 trifluoro-acetamide: To the ice-cold trifluoroacetic anhydride (60 mL) was added 4-amino-3-methyl-benzonitrile (14.33 g, 0.108 mol)

in portion. The resulting white slurry was stirred at 0° C. for 30 min. Then ammonium nitrate (17.28 g, 0.216 mol) was added. The reaction mixture was allowed to stir at 0° C. for 1 h and at room temperature for 14 h. After removal of most solvent, the reaction mixture was cooled with ice and quenched with ice. The yellow precipitate was filtered, washed with cold water, and dried under vacuum. The crude product (15.5 g, 52% yield, and ca. 80% pure) was used for the next step without purification. $^1$H NMR (300 MHz, CD$_3$OD) δ 8.05 (1H, s), 7.74 (1H, s), 2.30 (3H, s). LRMS (neg. ESI, (M−H)$^−$) m/z 272.

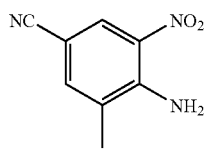

4-Amino-3-methyl-5-nitro-benzonitrile: A mixture of N-(4-cyano-2-methyl-6-nitro-phenyl)-2,2,2-trifluoro-acetamide (5 g, 18.3 mmol) and 2 M ammonia in methanol (80 mL) was heated to reflux for 14 h and then cooled to room temperature. After concentration in vacuo, the residue was purified by flash chromatography (20% EtOAc/hexane) to yield the title compound (3.24 g, 100%, ca 80% pure). $^1$H NMR (300 MHz, CDCl$_3$) δ 8.40 (1H, s), 7.47 (1H, s), 6.6-6.8 (2H, broad s), 2.89 (3H, s).

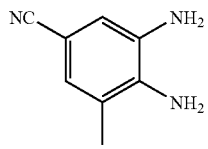

3,4-Diamino-5-methyl-benzonitrile: To a solution of 4-amino-3-methyl-5-nitro-benzonitrile (3.24 g, 18.3 mmol) in ethanol (80 mL) was added tin chloride dihydrate (8.67 g, 49.75 mmol). The reaction mixture was heated to reflux for 14 h, then cooled to room temperature, and concentrated in vacuum. The residue was diluted with ethyl acetate (100 mL) and treated with triethylamine (20 mL). The resulting slurry was filtered through a pad of celite and the filtercake was rinsed with three-portion ethyl acetate (50 mL). The filtrate was washed with saturated NaHCO$_3$, water, and brine, then dried over Na$_2$SO$_4$ and filtered. After removal of solvent, the residue was purified by flash chromatography on silica gel (30%-50% EtOAc/hexane) to yield the title compound (2.17 g, 81%) as a light yellow solid. $^1$H NMR (300 MHz, CDCl$_3$) δ 6.94 (1H, s), 6.85 (1H, s), 2.16 (3H, s). LCMS (M+H)$^+$ m/z 148 (t=0.67 min.).

Procedure for the Preparation of 5-bromo-3-methyl-benzene-1,2-diamine

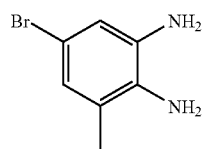

5-Bromo-3-methyl-benzene-1,2-diamine: To a suspension of 4-bromo-2-methyl-6-nitro-phenylamine (20 g, 0.086 mol) in ethanol (200 mL) was added tin chloride dihydrate (49.2 g, 0.258 mol). The reaction mixture was heated to reflux for 14 h, cooled to room temperature, and concentrated in vacuo. The residue was diluted with ethyl acetate (150 mL) and treated with triethylamine (40 mL). The resulting slurry was filtered through a pad of celite, and the filtercake was rinsed with three portions ethyl acetate (50 mL). The filtrate was washed with saturated NaHCO$_3$, water, and brine, then dried over Na$_2$SO$_4$ and filtered. After removal of the solvent, the residue was purified by flash chromatography on silica gel (30% EtOAc/hexane, then 5% MeOH/CH$_2$Cl$_2$) to yield the title compound (10.26 g, 59%) as a yellow oil. $^1$H NMR (300 MHz, CDCl$_3$) δ 6.77 (1H, d, J=2.0 Hz), 6.74 (1H, d, J=2.0 Hz), 2.16 (3H, s). LCMS (M+H)$^+$ m/z 201. (t=0.83 min.).

Procedure for the preparation of 1-[4-(3,4-diamino-5-methyl-phenyl)-piperazin-1-yl]-ethanone

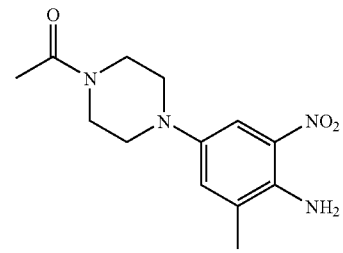

1-[4-(4-Amino-3-methyl-5-nitro-phenyl)-piperazin-1-yl]-ethanone: A mixture of 4-bromo-2-methyl-6-nitro-phenylamine (5 g, 21.64 mmol), 1-acetylpiperazine (4.2 g, 32.46 mmol), palladium acetate (244 mg, 1.08 mmol), tri-tert-butylphosphine (440 mg, 2.16 mmol) and sodium tert-butoxide (4.2 g, 43.29 mmol) in toluene (70 mL) was heated to 100° C. for 14 h under nitrogen. The reaction mixture was cooled to room temperature and diluted with EtOAc. After extraction, the combined organic layers were washed with water, brine, dried over Na$_2$SO$_4$. Concentration gave a brownish residue which was purified by flash column chromatography (10% MeOH/CH$_2$Cl$_2$) to yield the title compound (4.21 g, 70%). $^1$H NMR (400 MHz, CD$_3$OD) δ 7.42 (1H, d, J=2.8 Hz), 7.23 (1H, d, J=2.8 Hz), 3.71 (2H, t, J=5.1 Hz), 3.67 (2H, t, J=5.1 Hz), 3.04 (2H, t, J=5.2 Hz), 2.98 (2H, t, J=5.2 Hz), 2.24 (3H, s), 2.31 (3H, s). LCMS (M+H)$^+$ m/z 279 (t=1.46 min.).

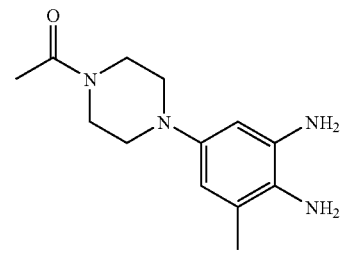

1-[4-(3,4-Diamino-5-methyl-phenyl)-piperazin-1-yl]-ethanone: To 1-[4-(4-amino-3-methyl-5-nitro-phenyl)-piperazin-1-yl]-ethanone (4.5 g, 16.2 mmol) and 10% palladium on carbon (400 mg) were added methanol (50 mL) and acetic acid (5 mL) under nitrogen. The reaction mixture was stirred under hydrogen atmosphere (hydrogen balloon) for 14 h. The dark solution was filtered through a pad of celite and the filtercake was washed with methanol. Concentration of the filtrate gave the title compound (4.00 g, 100%) which was used for the next step without purification. LCMS (M+H)+ m/z 207 (t=0.41 min.).

Procedure for the Preparation of 5-fluoro-3-methyl-2-nitro-aniline:

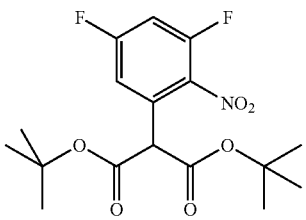

2-(3,5-Difluoro-2-nitro-phenyl)-malonic acid di-tert-butyl ester: To a suspension of NaH (54.6 g, 60%, 1.365 mol) in 600 mL of DMF was added di-t-Butyl malonate (118 g, 0.546 mol) at 0° C. and stirred for 30 min. 2,4,6 trifluoronitrobenzene was added as a solution in 400 mL of DMF (75 g, 0.42 mol) over 3 hours and the solution stirred at ambient temperature for 12 hours. The reaction mixture was extracted with ethyl acetate (3X's). The ethyl acetate was washed with water (3X's) and with brine and dried over MgSO$_4$ and concentrated to give 62 g of crude product. LCMS [M+Na]-396; $^1$H NMR (500 MHz, DMSO) δ 7.81 (m, 1H), 7.27 (m, 1H), 5.00 (s, 1H), 1.41 (m, 18H).

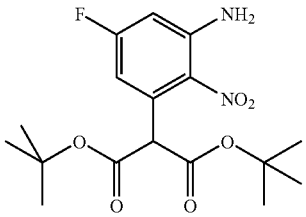

2-(3-Amino-5-fluoro-2-nitro-phenyl)-malonic acid di-tert-butyl ester: To the crude 2-(3,5-Difluoro-2-nitro-phenyl)-malonic acid di-tert-butyl ester (62 g, 0.42 mol) was added 700 mL of 2M ammonia in methanol in a pressure bottle. The vessel was sealed and heated to 85° C. for 18 hours. The reaction mixture was cooled and the vessel opened carefully and the methanol solution concentrated to provide 140 g of crude material. LCMS [M+Na]-393; $^1$H NMR (500 MHz, DMSO) δ 6.76 (dd, J=10.8 2.8 Hz, 1H), 6.29 (dd, J=10.8, 2.8 Hz, 1H), 4.99 (brs, 2H), 4.80 (s, 1H), 1.40 (m, 18H).

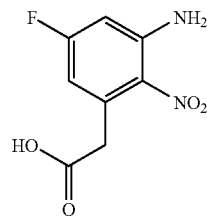

3-Amino-5-fluoro-2-nitro phenyl acetic acid: To the 2-(3-Amino-5-fluoro-2-nitro-phenyl)-malonic acid di-tert-butyl ester (140 g) in 500 mL of 4N HCl in dioxane was added 50 mL of water and heated to 40° C. for 2 days. The solution was extracted with ethyl acetate (3X's) and the ethyl acetate washed with water (3X's) and brine. The organic fraction was dried over MgSO$_4$ and was concentrated to give 78 g of crude (66% pure by LC/MS); $^1$H NMR (500 MHz, DMSO) δ 12.40 (brs, 1H), 7.04 (s, 2H), 6.68 (dd, J=10.92.8 Hz, 1H), 6.47 (dd, J=10.9, 2.8 Hz, 1H), 3.80 (s, 2H).

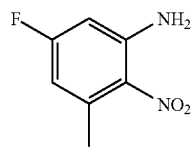

5-Fluoro-3-methyl-2-nitro-aniline: To the crude 3-amino-5-fluoro-2-nitro phenyl acetic acid (3.6 g, 16.8 mmol) was added Cu$_2$O (10.1 g, 70.6 mmol) in 120 mL of acetonitrile along with 50 uL of methanol and the suspension was refluxed for 12 hours. The reaction mixture was filtered through Celite and the Celite pad washed with water and ethyl acetate. The filtrate was extracted with ethyl acetate, washed with water and brine, dried over Na$_2$SO$_4$ and concentrated to give 2.95 g of material which by $^1$H NMR was 80% pure. ESIMS [M+Na]-193; $^1$H NMR (500 MHz, DMSO) δ 6.67 (s, 2H), 6.56 (dd, J=11, 2.8 Hz, 1H), 6.39 (dd, J=11, 2.8 Hz, 1H), 2.50 (s, 3H).

Procedure for the Preparation of 2-methyl-4-morpholin-4-yl-6-nitro-phenylamine

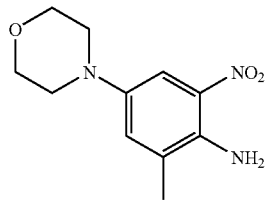

2-Methyl-4-morpholin-4-yl-6-nitro-phenylamine: To a 800 ml pressure flask was added tris(dibenzylideneacetone)dipalladium (2.64 g, 2.88 mmol), 2-(di-t-butylphosphino)biphenyl (1.42 g, 4.75 mmol) and sodium tert-butoxide (17.5 g, 182 mmol). Then dry THF (500 mL), 4-bromo-2-ethyl-6-nitroaniline (30.0 g, 130 mmol) and morpholine (34 ml, 390 mmol) were added. Argon was bubbled through the solution for 1 minute and the flask was sealed. The reaction mixture was stirred at 85° C. for 3 days. THF was evaporated in vacuo and the crude product was preabsorbed on silica and this then transferred on top of a silica gel column. Elution with hexane-ethyl acetate (6:4 to 4:6 to 0:1 gradient) gave, after evaporation of solvents, the title compound (15.2 g red-brown solid, 49.3%). LCMS (M+H)+ m/z 238 (t=0.64 min.) $^1$H NMR (500 MHz, DMSO-d$_6$) δ 7.32 (1H, s), 7.22 (1H, s), 6.96 (2H, s), 3.72 (4H, broad s), 2.96 (4H, broad s), 2.21 (3H, s).

Procedure for the Preparation of 4-(3-amino-5-methyl-4-nitro-phenyl)-piperazine-1-carboxylic acid tert-butyl ester

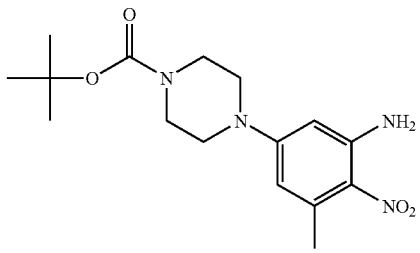

4-(3-Amino-5-methyl-4-nitro-phenyl)-piperazine-1-carboxylic acid tert-butyl ester: To a stirred solution of 3-fluoro-5-amino-6-nitrotoluene (10 g, 58.79 mmol) in anhydrous NMP (160 mL) under nitrogen was added BOC-piperazine (39 g, 209.4 mmol) and 4-methylmorpholine (25.9 mL). The resulting dark solution was heated to reflux for 72 h, cooled to room temperature and diluted with ethyl acetate (4000 mL). The organic layer was washed with water (8×1500 mL), brine (1×1500 mL), dried over sodium sulfate and evaporated in vacuo. The resulting dark oil was dissolved in boiling absolute ethanol (800 mL) and concentrated to a total volume of 400 mL and left to stand overnight at room temperature. The solution was further cooled to −20° C. for 5 h and the resulting solid was filtered off and dried in vacuo to give 16.3 g (83%) of a light yellow solid. $^1$H NMR (500 MHz, CDCl$_3$) δ 6.16 (brs, 1H), 6.04 (brs, 1H), 3.70-3.60 (m,4H), 3.38-3.25 (m, 4H), 2.53 (s, 3H), 1.48 (s, 9H); LCMS (M+H)$^+$ m/z 337.

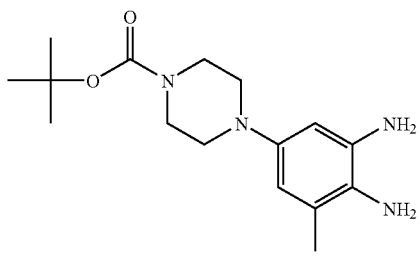

4-(3,4-Diamino-5-methyl-phenyl)-piperazine-1-carboxylic acid tert-butyl ester:

To a stirred solution of 4-(3-Amino-5-methyl-4-nitrophenyl)-piperazine-1-carboxylic acid tert-butyl ester (15 g, 44.6 mmol) in methanol (2200 mL) was added 20% Pd(OH)$_2$/C (1.6 g) and the suspension flushed well with nitrogen, followed by hydrogen. The resulting suspension was stirred overnight at room temperature under an atmosphere of hydrogen (ca. 1 atm). The resulting suspension was filtered under nitrogen through a pad of Celite and washed with methanol (400-500 mL). The resulting material was used immediately. LCMS (M+H)$^+$ m/z 307.

Procedure for the Preparation of [1-(3-amino-5-methyl-4-nitro-phenyl)-piperidin-4-yl]-carbamic acid tert-butyl ester

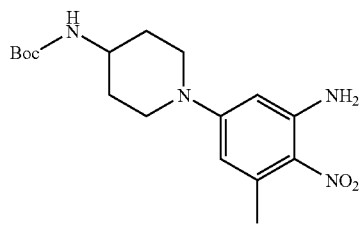

[1-(3-Amino-5-methyl-4-nitro-phenyl)-piperidin-4-yl]-carbamic acid tert-butyl ester: 5-Fluoro-3-methyl-2-nitro-phenylamine (0.97 g, 5.7 mmol), 4-N-BOC-aminopiperidine (1.60 g, 8.0 mmol), diisopropylethylamine (2.5 ml, 14 mmol) and DMSO (10 ml) are combined and stirred at 85° C. for 3 hours. The reaction mixture was poured on saturated aqueous NaHCO$_3$ solution and extracted with ethyl acetate. The organic layers were washed with water (3×) and brine, dried over Na$_2$SO$_4$ and concentrated. Flash column chromatography on silica (eluent hexanes-ethyl acetate-triethylamine 50-50-1, then 33-66-1) gave the tiitle compound as a yellow solid. (1.57 g, 79%). LCMS (M+H)$^+$ m/z 351 (t=1.55 min.). $^1$H NMR (500 MHz, CD$_3$OD) δ 6.70 (1H, broad s), 6.22 (1H, d, J=2.5 Hz)), 6.13 (1H, d, J=2.5 Hz), 3.88 (2H, d, J=13.3 Hz), 3.58 (1H, broad s), 2.98 (2H, t, J=11.8 Hz), 2.48 (3H, s), 1.92 (2H, d, J=11.3 Hz), 1.48 (2H, m), 1.45 (9H, s).

Procedure for the Preparation of 3-methyl-5-(2-morpholin-4-ethoxy)-2-nitro phenylamine

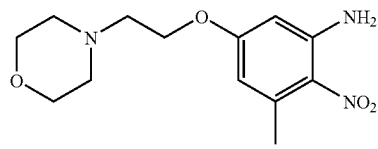

3-Methyl-5-(2-morpholin-4-ethoxy)-2-nitro phenylamine: To a solution of 2-morpholin-4-yl-ethanol (5 g, excess) in THF (30 mL) was added NaH (0.21 g, 8.82 mmol) in portion under ice bath. The reaction mixture was stirred at room temperature for 30 min. Then 5-fluoro-3-methyl-2-nitrophenylamine was added. The reaction mixture was heated to reflux for 6 h, cooled to room temperature, and concentrated. The residue was diluted with water and extracted with EtOAc. The combined organic layers were washed with water, brine, and dried over Na$_2$SO$_4$. After concentration, the residue was purified by column chromatography (20% EtOAc/hexane) to yield the title compound (0.70 g, 85%). $^1$H NMR (400 MHz, CD$_3$OD) δ 6.10 (1H, s), 6.09 (1H, s), 4.38-4.42 (2H, m), 3.92-4.08 (4H, m), 3.72 (1H, d, J=12 Hz), 3.53-3.56 (2H, m), 3.05-3.10 (2H, m), 2.48 (3H, s). LCMS (M+H)$^+$ m/z 282 (t=0.73 min.).

Procedure for the Preparation of 5-(1,4,5,6-tetrahydropyrimidin-1-yl)-3-methyl-2-nitro aniline

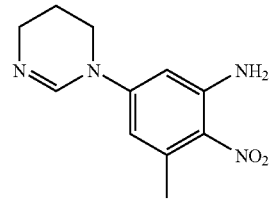

5-(1,4,5,6-Tetrahydropyrimidin-1-yl)-3-methyl-2-nitro aniline: To a stirred solution of 2.0 g (11.76 mmol) of 5-fluoro-3-methyl-2-nitro-aniline in 10 mL of DMSO was added 1.2 g (14.11 mmol) of 1,4,5,6-tetrahydropyrimidine, and 2.43 g (17.64 mmol) of potassium carbonate, and the mixture was heated at 100° C. for 10 hrs, cooled, diluted with water, and extracted with Ethylacetate containing 5% methanol. The combined organic extract was washed with water, brine and dried (Na$_2$SO$_4$). Evaporation of the solvent furnished the residue, which was chromatographed (20% of 2M ammonia in methanol and dichloromethane) to produce 1.85 g (67%) of the product as red solid. $^1$H NMR (400 MHz, CD$_3$OD) δ 7.89 (1H, s), 6.53 (1H, d, J=2.57 Hz), 6.44 ((1H, d, J=2.1 Hz), 7.04 (1H, d, J=2.1 Hz), 3.70 (2H, t, J=6.0 Hz), 3.41 (2H, t, J=5.65 Hz), 2.43 (3H, s), 2.05 (2H, m) LCMS (M+H)$^+$ m/z 235 (t=0.78 min).

Procedure for the Preparation of 2-(5-chloro-3,6-dimethoxy-pyridazin-4-yl)-4-methyl-6-morpholin-4-yl-1H-benzimidazole

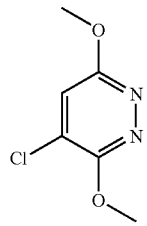

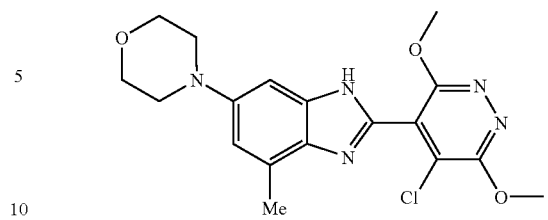

4-Chloro-3,6-dimethoxy-pyridazine: A solution of n-butyllithium (1.6 M in hexanes, 2.45 mL, 3.92 mmol) was added to a cold solution of THF (20 mL) at −78° C. Tetramethylpiperidine (0.67 mL, 3.92 mol) was introduced and the solution was warmed to 0° C. and kept at this temperature for 20 min; it was then cooled to −78° C. A solution of 3,6-dimethoxy-pyridazine (500 mg, 3.57 mmol) in THF (5 mL) was added slowly and the mixture was stirred at −78° C. for 45 min. This reaction mixture was transferred to a solution of achloroethane (1.268 g, 5.36 mmol) in THF (10 mL) at −78° C. and stirring was continued at −78° C. for 15 min. Saturated aqueous $NH_4Cl$ was added and the mixture was warmed to room temperature. The mixture was extracted with EtOAc, dried over $MgSO_4$, and concentrated in vacuo to give the crude product, which was purified by flash chromatography, eluting with 10-20% EtOAc in hexanes to afford, after evaporation, the title compound as a white solid (372 mg, 60%): $^1$H NMR (400 MHz, DMSO) δ 7.04 (s, 1H), 4.11 (s, 3H), 4.04 (s, 3H); LCMS ($^+$ESI, M+H$^+$) m/z 175.

2-(5-Chloro-3,6-dimethoxy-pyridazin-4-yl)-4-methyl-6-morpholin-4-yl-1H-benzimidazole: To a stirred solution of 2-methyl-4-morpholin-4-yl-6-nitro-phenylamine (0.252 g, 1.06 mmol) in methanol (15 mL) was added 10% palladium on carbon (25 mg) and the suspension flushed well with nitrogen, followed by hydrogen. The resulting suspension was stirred 8 hours at room temperature under an atmosphere of hydrogen (ca. 1 atm). The resulting suspension was filtered under nitrogen through a pad of Celite and washed with methanol (25 mL). This solution was cooled down to 0° C., the 5-chloro-3,6-dimethoxy-pyridazine-4-carbaldehyde (0.225 g, 1.12 mmol) in methanol (10 mL) was added and the reaction mixture was stirred exposed to air at 23° C. for 18 hours. MeOH was evaporated in vacuo and the crude material was purified by preparative HPLC (see method below) to give the title compound as a yellow solid. (0.265 g, 64%) HPLC: 99% (220 nm), LCMS ($^+$ESI, M+H$^+$) m/z 390, IR (KBr, cm$^{-1}$) 3421, 2956, 2852, 1625, 1470, 1362; $^1$H NMR (400 MHz, CDCl$_3$) δ 9.99 (s, 1H), 7.17 (s, 0.3H) 6.88 (s, 0.3H), 6.80 (s, 0.7H), 6.74 (s, 0.7H), 4.14 (s, 0.9H), 4.13 (s, 0.9H), 4.12 (s, 2.2H), 4.11 (s,2.2H), 3.83 (m, 4H), 3.13 (m, 4H), 2.62 (s, 2.2H), 2.48 (s, 0.9H).

Procedure for the Preparation of 2-(4-chloro-2,6-dimethoxy-pyrimidin-5-yl)-4-methyl-6-morpholin-4-yl-1H-benzimidazole

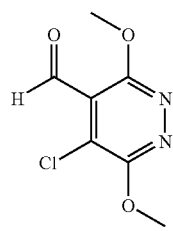

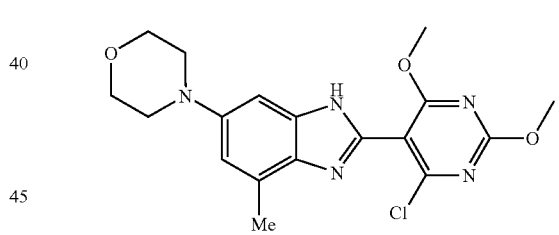

5-Chloro-3,6-dimethoxy-pyridazine-4-carbaldehyde: A solution of n-butyllithium (1.6 M in hexanes, 0.39 mL, 0.63 mmol) was added to a cold solution of THF (10 mL) at −78° C. Tetramethylpiperidine (0.11 L, 0.63 mmol) was introduced and the solution was warmed to 0° C. and kept at this temperature for 20 min; it is then cooled to −78° C. A solution of 4-chloro-3,6-dimethoxy-pyridazine (100 mg, 0.57 mmol) in 20 THF (5 mL) was added slowly and the mixture was stirred at −78° C. After stirring for 45 min at −78° C., ethyl formate (0.07 mL, 0.86 mmol) was added and stirring was continued at −78° C. for 15 min. Saturated aqueous $NH_4Cl$ was added and the mixture was warmed to room temperature. The mixture was extracted with EtOAc, dried over $MgSO_4$, and concentrated in vacuo to give the crude product, which was purified by flash chromatography, eluting with 20-30% EtOAc in hexanes to afford, after evaporation, the title compound as a light yellow solid (51 mg, 44%): IR (KBr, cm$^{-1}$) 1702, 1474, 1388, 1022; $^1$H NMR (400 MHz, DMSO) δ 10.36 (s, 1H), 4.17 (s, 3H), 4.16 (s, 3H); LCMS ($^+$ESI, M+H$^+$) m/z 203.

2-(4-Chloro-2,6-dimethoxy-pyrimidin-5-yl)-4-methyl-6-morpholin-4-yl-1H-benzoiniidazole: To a stirred solution of 2-methyl-4-morpholin-4-yl-6-nitro-phenyl amine (0.290 g, 1.22 mmol) in methanol (40 mL) was added 10% palladium on carbon (180 mg) and the suspension flushed well with nitrogen, followed by hydrogen. The resulting suspension was stirred 8 hours at room temperature under an atmosphere of hydrogen (ca. 1 atm). The resulting suspension was filtered under nitrogen through a pad of Celite and washed with methanol (50 mL). This solution was cooled down to 0° C. and the 4-chloro-2,6-dimethoxy-pyrimidine-5-carbaldehyde (N. Ple et al. *J. Heterocyclic Chem.*, 28, 283, 1991 (0.272 g, 1.34 mmol) in methanol (50 ml) was added and the reaction mixture as stirred exposed to air at 23° C. for 18 hours. MeOH was evaporated in vacuo and the crude material was purified on silicagel dry column using $CH_2Cl_2$: Isopropanol (9:1) to give the title compound as a yellow solid. (0.304 g, 64%), HPLC: 98% (220 nm), LCMS ($^+$ESI, M+H$^+$) m/z 390, IR (KBr, cm$^{-1}$) 3421, 2955, 2854, 1602, 1540, 1385; $^1$H NMR (400 MHz, DMSO) δ 6.70 (br s, 2H), 3.87 (s, 3H), 3.80 (s, 3H), 3.63 (m, 4H), 2.94 (m, 4H), 2.34 (s, 3H); HRMS calcd for $C_{18}H_{20}ClN_5O_3$: 389.12547; found 389.12557.

Procedure for the Preparation of S)-(2E and 2Z)-2-[2-(3-chloro-phenyl)-2-hydroxy-ethylamino]-3-(1-tert-butyloxycarbonyl-4-methyl-6-morpholin-4-yl-1H-benzoimidazol-2-yl)-but-2-enedioic acid diethyl ester

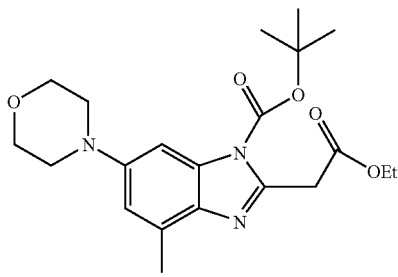

(1-Tert-butyloxycarbonyl-4-methyl-6-morpholin-4-yl-1H-benzoimidazole-2-yl)-acetic acid ethyl ester: A solution of 2-methyl-4-morpholin-4-yl-6-nitro-phenylamine (1.84 g, 7.75 mmol) in methanol (115 mL) was hydrogenated (15 psi) in presence of palladium(II) hydroxide for 12 hours. The reaction was filtered and the filtrate was evaporated. The crude amine was dissolved in N,N-dimethylformamide (70 mL) and treated with the hydrochloride salt of ethyl monoimido malonate (3.04 g, 15.48 mmol) and this mixture was stirred at 70° C. for 2 hours. The solvent was evaporated and the residue was dissolved in dichloromethane (100 mL) and treated with triethylamine (2.16 mL, 15.48 mmol), di-tert-butyl dicarbonate (3.38 g, 15.48 mmol) and dimethylaminopyridine (2 crystals). The reaction was stirred at RT for 1.5 hours, then saturated ammonium chloride was added and the mixture was extracted with ethyl acetate (3x). The combined organic layers were dried over anhydrous magnesium sulfate, filtered and concentrated. The residue was purified by silica gel column chromatography (50% ethyl acetate in hexane) to give the title material (1.955 g, 63%) as a brown solid. LCMS (⁺ESI, M+H⁺) m/z 404; ¹H NMR (400 MHz, DMSO-d₆) δ (ppm): 1.26 (3H, t, J=7.1 Hz), 1.70 (9H, s), 2.56 (3H, s), 3.21 (4H, br dd), 3.85 (4H, br dd), 4.18 (2H, qa, J=7.1 Hz), 4.27 (2H, s), 7.02 (1H, d, J~1.5 Hz), 7.33 (1H, d, J=2.0 Hz).

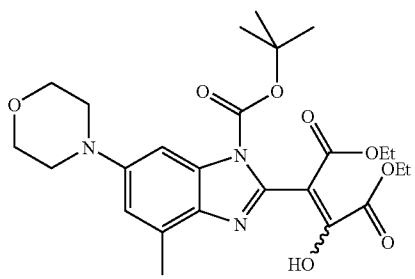

2-(1-Tert-butyloxycarbonyl-4-methyl-6-morpholin-4-yl-1H-benzoimidazol-2-yl)-3-oxo-succinic acid diethyl ester: To a stirred solution of bis(trimethylsilylamide) (1M in THF, 1.04 mL, 1.04 mmol) in tetrahydrofuran (0.5 mL) was added a solution of (1-tert-butyloxycarbonyl-4-methyl-6-morpholin-4-yl-1H-benzoimidazol-2-yl)-acetic acid ethyl ester (0.200 g, 0.496 mmol) in tetrahydrofuran (2.5 mL) at −78° C. The solution was stirred at −78° C. for 45 minutes then saturated ammonium chloride was added and the mixture was allowed to reach RT. Ethyl acetate was added and the phases were separated. The aqueous phase was extracted with ethyl acetate (3x) and the combined organic phases were washed with brine, dried over anhydrous magnesium sulfate, filtered and concentrated. The residue was purified by silica gel chromatography (ethyl acetate then 10% acetic acid in ethyl acetate) to give the title material (0.218 g, 87%) as a brownish solid. HPLC: 92% (220 nm), LCMS (⁺ESI, M+H⁺) m/z 504; ¹H NMR (400 MHz, DMSO-d₆) δ (ppm): 1.12 (3H, t, J=7.1 Hz), 1.24 (3H, t, J=7.1 Hz), 1.55 (9H, s), 1.80 (3H, s), 3.13 (4H, br dd), 3.75 (4H, br dd), 4.02 (2H, br qa), 4.15 (2H, qa J=7.1 Hz), 7.03 (1H, br s), 7.13 (1H, s).

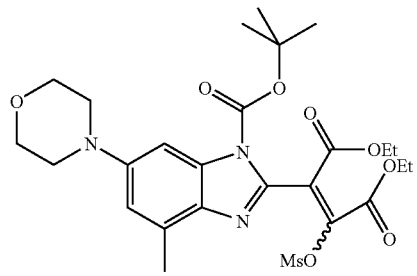

(2-E and 2Z)-2-Methanesulfonyloxy-3-(1-tert-butyloxycarbonyl-4-methyl-6-morpholin-4-yl-1H-benzoimidazol-2-yl)-but-2-enedioic acid diethyl ester: To a stirred solution of 2-(1-tert-butyloxycarbonyl-4-methyl-6-morpholin-4-yl-1H-benzoimidazol-2-yl)-3-oxo-succinic acid diethyl ester (0.206 g, 0.409 mmol) in dichloromethane (5 mL) at 0° C. was added methanesulfonyl chloride (47 μL, 0.614 mmol) and triethylamine (97 μL, 0.695 mmol). The mixture was stirred for 0.5 hours, then triethylamine (25 μL) and methanesulfonyl chloride (12 μL) were added twice again until the reaction was completed. Water was added and the phases were separated. The aqueous phase was extracted with dichloromethane (3x) and the combined organic layers were dried over anhydrous magnesium sulfate, filtered and concentrated. The residue was purified by silica gel chromatography (50% ethyl acetate in hexane) to give the title material (0.170 g, 71%) as a bright yellow solid. LCMS (⁺ESI, M+H⁺) m/z 582; ¹H NMR (400 MHz, DMSO-d₆) δ (ppm): 1.13 and 1.15 (3H, 2t, J=7.1 Hz), 1.25 and 1.28 (3H, 2t, J=7.1 Hz), 1.58 (9H, 2s), 2.07, 2.32, 2.43, 2.45 and 2.47 (6H, 5s overlapped by DMSO-d₆), 3.15 (4H, m), 3.76 (4H, m), 4.15 (2H, m), 4.23-4.32 (2H, m), 7.0 and 7.02 (1H, 2 br s), 7.18 and 7.22 (1H, 2d, J=2.0 Hz).

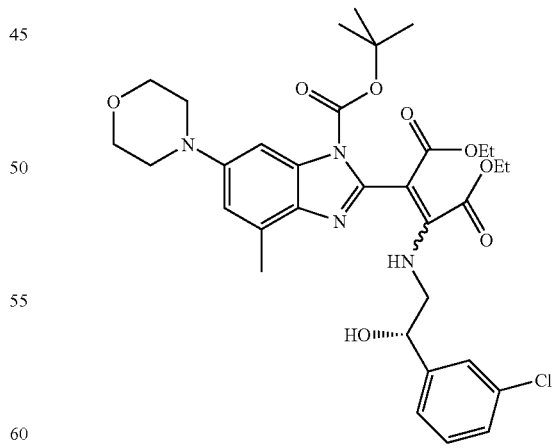

(S)-(2E and 2Z)-2-[2-(3-Chloro-phenyl)-2-hydroxy-ethylamino]-3-(1-tert-butyloxycarbonyl-4-methyl-6-morpholin-4-yl-1H-benzoimidazol-2-yl)-but-2-enedioic acid diethyl ester: To a stirred solution of (2-E and 2Z)-2-methanesulfonyloxy-3-(1-tert-butyloxycarbonyl-4-methyl-6-morpholin-4-yl-1H-benzoimidazol-2-yl)-but-2-enedioic acid diethyl ester (0.012 g, 0.021 mmol) in acetonitrile (1 mL) was added (S)-2-amino-1-[3-chlorophenyl]ethanol (0.005 g, 0.031 mmol) and the mixture was stirred at 60° C. for 1 hour. The solvent was evaporated and the residue was purified by silica gel chromatography (50 to 75% ethyl acetate in hexane) to give the title material (0.010 g, 74%). HPLC: 97% (220 nm), LCMS ($^+$ESI, M+H$^+$) m/z 657; $^1$H NMR (400 MHz, acetone-d$_6$) δ (ppm): 1.17-1.33 (15H, m), 2.51 (3H, br s), 3.14 (4H, m), 3.77 (6H, m), 4.24-4.34 (4H, m), 5.62 (1H, m), 6.80-7.52 (6H, m).

Example 1

Preparation of 6-[2-(3-chloro-phenyl)-2-hydroxy-ethylamino]-5-(4-methyl-6-morpholin-4-yl-1H-benzoimidazol-2-yl)-1H-pyrimidine-2,4-dione

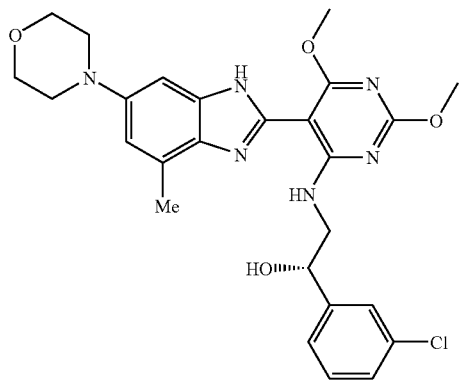

1-(3-chloro-phenyl)-2-[2,6-dimethoxy-5-(4-methyl-6-morpholin-4-yl-1H-benzoimidazol-2-yl)-pyrimidin-4-ylamino]-ethanol: To a solution of 2-(4-chloro-2,6-dimethoxy-pyrimidin-5-yl)-4-methyl-6-morpholin-4-yl-1H-benzoimidazole (0.075 g, 0.192 mmol) in acetonitrile (5 mL) was added triethylamine (134 μl, 0.962 mmol) and (S)-2-Amino-1-(3-chloro-phenyl)-ethanol hydrochloride (42 mg, 0.202 mmol). The crude material was purified on silicagel dry colomn using AcOEt: Hex (8:2) to give the title compound as a beige solid. (0.055 g, 55%). HPLC 98%. LCMS 20 ($^+$ESI, M+H$^+$) m/z 525. IR (KBr, cm$^{-1}$) 3446, 2955, 1595, 1472, 1367. $^1$H NMR (400 MHz, DMSO) δ 11.63 (s, 1H), 11.1 (m, 1H), 7.54 (s, 1H), 7.41-7.28 (m, 3H), 6.87 (d, J=2.0 Hz, 1H), 6.78 (s, 1H) 5.85 (s. 1H), 4.88 (m, 1H), 4.05 (s, 3H), 3.91-3.84 (m, 4H), 3.79-3.77 (m, 4H), 3.73-3.69 (m, 1H), 3.09-3.07 (m, 4H), 2.50 (3H, s). HRMS calcd for C$_{26}$H$_{29}$ClN$_6$O$_4$: 525.2017; found 525.2008.

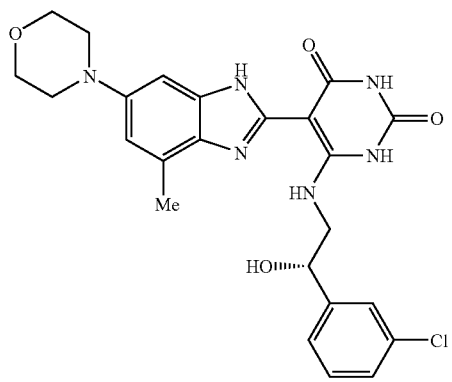

6-[2-(3-Chloro-phenyl)-2-hydroxy-ethylamino]-5-(4-methyl-6-morpholin-4-yl-1H-benzoimidazol-2-yl)-1H-pyrimidine-2,4-dione: A solution of 1-(3-chloro-phenyl)-2-[2,6-dimethoxy-5-(4-methyl-6-morpholin-4-yl-1H-benzoimidazol-2-yl)-pyrimidin-4-ylamino]-ethanol (0.041 g, 0.078 mmol) in a mixture of AcOH (17.4 M) and HCl (11.6 M: (1.3 mL: 1.0 mL) was stirred in a sealed tube at 55° C. for 18 hours. Then solvents were evaporated in vacuo and the crude material was purified by preparative HPLC (see method below) to give the title compound as a beige solid (29 mg, 77%), HPLC 99%. LCMS ($^+$ESI, M+H$^+$) m/z 497. IR (KBr, cm$^{-1}$) 3420, 2961, 2856, 1717, 1635, 1559; $^1$H NMR (400 MHz DMSO) δ 11.88 (s, 2H), 10.84 (s, 1H), 7.58 (s, 1H), 7.46-7.30 (m, 3H), 6.97 (d, J=2 Hz, 1H), 6.68 (s, 1H), 6.10 (br s, 1H), 4.90 (m, 1H), 3.89 (m, 1H), 3.76 (m, 4H), 3.61 (m, 1H), 3.04 (m, 4H), 2.49 (3H, s); HRMS calcd for C$_{24}$H$_{25}$ClN$_6$O$_4$:497.1704; found 497.1698.

Example 2

Preparation of 4-[2-(3-chloro-phenyl)-2-hydroxy-ethylamino]-5-(4-methyl-6-morpholin-4-yl-1H-benzoimidazol-2-yl)-1,2-dihydro-pyridazine-3,6-dione

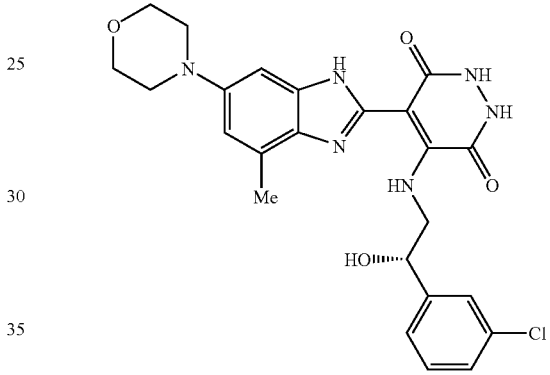

To 2-(5-chloro-3,6-dimethoxy-pyridazin-4-yl)-4-methyl-6-morpholin-4-yl-1H-benzoimidazole (0.145 g, 0.372 mmol) was added concentrated HBr (48%, 10 mL). The reaction mixture was stirred in a sealed tube at 85° C. for 6 hours. Then HBr solution was evaporated in vacuo. The crude material was used without more purification for the next reaction ($^+$ESI, M+H$^+$) m/z 406. To the crude bromodihydropyridazinedione obtained was added acetonitrile (10 mL), triethylamine (1.04 mL, 7.44 mmol) and (S)-2-Amino-1-(3-chloro-phenyl)-ethanol hydrochloride (83 mg, 0.409 mmol). The reaction mixture as stirred in a sealed tube at 90° C. for 8 hours. The solvent was removed in vacuo. A saturated NaHCO$_3$ solution (50 mL) was added to the crude material and the target compound was extracted with AcOEt: THF (4:1) (3×30 mL). The combined organic layers, were dried over MgSO$_4$, concentrated and the solid obtained was purified by crystallization in hot isopropanol (3 mL) to give the title compound as a light brown solid. (35 mg, 19%). HPLC 97%. LCMS ($^+$ESI, M+H$^+$) m/z 497; IR (KBr, cm$^{-1}$) 3384, 2958, 28577, 1617, 1473, 1259;

$^1$H NMR (400 MHz, DMSO) δ 12.9-12.7 (br s, 1H), 11.5-11.2 (br s, 2H), 7.5 (s, 1H), 7.38-7.26 (m, 3H), 7.02 (s, 1H), 6.78 (s, 1H), 4.84 (m, 1H), 4.22 (m, 1H), 3.92 (m, 1H), 3.77 (m, 4H), 3.07 (m, 4H), 2.5 (s, 3H); HRMS calcd for C$_{24}$H$_{25}$ClN$_6$O$_4$:496.1626; found 496.1625.

Preparative HPLC Method:

Purification Method: Initial gradient (15% B, 85% A) ramp to final gradient (100% B, 0% A) over 7 minutes, hold for 3 minutes (100% B, 0% A)

Solvent A: 10% CH₃CN/90% H₂O/5 mmol NH₄OAc
Solvent B: 10% H₂O/90% CH₃CN/5 mmol NH₄OAc
Column: YMC C18 S5 20×100 mm column Example 3

Preparation of (S)-3-[2-(3-chloro-phenyl)-2-hydroxy-ethylamino]-4-(4-methyl-6-morpholin-4-yl-1H-benzoimidazol-2-yl)-pyrrole-2,5-dione

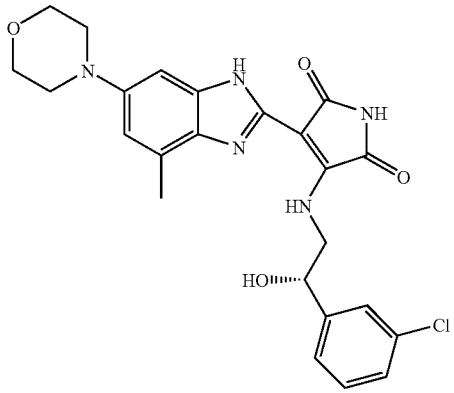

(S)-(2E and 2Z)-2-[2-(3-Chloro-phenyl)-2-hydroxy-ethylamino]-3-(1-tert-butyloxycarbonyl-4-methyl-6-morpholin-4-yl-1H-benzoimidazol-2-yl)-but-2-enedioic acid diethyl ester (0.014 g, 0.021 mmol) was dissolved in trifluoroacetic acid/dichloromethane (20%, 3 mL) and the reaction was stirred at RT for 1 hour. The solvent was evaporated and the residue was dissolved in ammonia (7N in methanol, 3 mL) and stirred in a sealed tube at ~50° C. for 3 hours. The solvent was evaporated and the residue was purified by Prep HPLC (ammonium acetate/water/acetonitrile) to give the title material (0.005 g, 50%) as a red solid. HPLC: 93% (220 nm), LCMS (⁺ESI, M+H⁺) m/z 482; IR v (cm⁻¹): 3420, 2922, 1652. ¹H NMR (400 MHz, DMSO-$d_6$) δ (ppm): 2.47 (3H, s), 3.05 (4H, m), 3.76 (4H, m), 3.90-3.97 (1H, m), 4.23-4.27 (1H, m), 4.90 (1H, m), 6.00 (1H, d, J=4.5 Hz) 6.74 (1H, br d), 6.85 (1H, br d), 7.32-7.50 (3H, m), 7.52 (1H, s), 9.38 (1H, t, J=5.1 Hz), 10.62 (1H, br s), 11.63 (1H, s).

Example 4

Preparation of (S) 3-[2-(3-chloro-phenyl)-2-hydroxy-ethylaminol]-1-methyl-4-(4-methyl-6-morpholin-4-yl-1H-benzoimidazol-2-yl)-pyrrole-2,5-dione

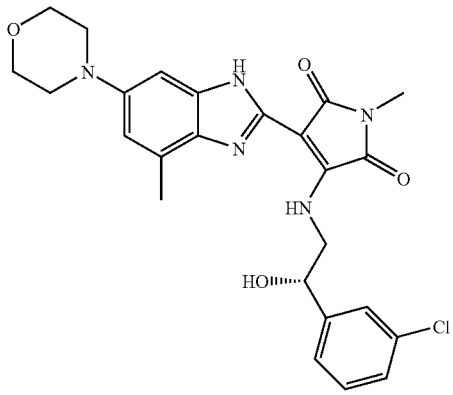

(S)-(2E and 2Z)-2-[2-(3-Chloro-phenyl)-2-hydroxy-ethylaminol]-3-(1-tert-butyloxycarbonyl-4-methyl-6-morpholin-4-yl-1H-benzoimidazol-2-yl)-but-2-enedioic acid diethyl ester (0.015 g, 0.023 mmol) was reacted as described for the synthesis of (S)-3-[2-(3-chloro-phenyl)-2-hydroxy-ethylamino]-4-(4-methyl-6-morpholin-4-yl-1H-benzoimidazol-2-yl)-pyrrole-2,5-dione to give the title material (0.003 g, 27%) as a red solid. HPLC: 89% (220 nm), LCMS (⁺ESI, M+H⁺) m/z 497; IR v (cm⁻¹): 3424, 2922, 1698, 1652. ¹H NMR (400 MHz, DMSO$d_6$) δ (ppm): 2.48 (3H, s), 2.92 (3H, s), 3.06 (4H, br dd), 3.77 (4H, br dd), 3.93-3.99 (1H, m), 4.26-4.30 (1H, m), 4.92 (1H, m), 6.03 (1H, d, J=4.3 Hz), 6.75 (1H, br d), 6.5 (1H, d, J=2.5 Hz), 7.32-7.43 (3H, m), 7.53 (1H, s), 9.51 (1H, d, J=2.1 Hz), 11.67 (1H, s).

It is understood that the examples described above in no way serve to limit the true scope of this invention, but rather are presented for illustrative purposes. All references cited herein are incorporated by reference in their entirety.

What is claimed is:

1. A compound of the formula:

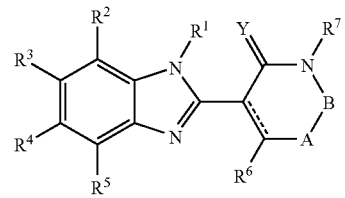

Y is O or S;
A is C=O, $C_1$-$C_3$ alkyl, NR⁷ or a direct bond;
B is C=O or NR⁷ provided that A and B are not both —NR⁷;
R¹, R², R⁴, R⁵, R⁶, and R⁷ are each independently selected from the group consisting of H, $C_{1-6}$ alkyl, alkenyl, alkynyl, cycloalkyl, halo, amino, aminoalkyl, alkoxy, thioalkoxy, nitro, aryl, alkoxyalkyl, thioalkoxyalkyl, aminoalkyl, aralkyl, —CN, —CO₂R⁸, —CONR⁹R¹⁰, —CO₂NR¹¹R¹², —NR¹³CONR¹⁴R¹⁵, —NR¹⁶SO₂R¹⁷, —SO₂NR¹⁸R¹⁹, —C(NR²⁰)NR²¹R²², —NH-Z, and —NH-Z-aryl;
R3 is morpholinyl;
Z is selected from the group consisting of $C_1$-$C_4$ alkyl, alkenyl, and alkynyl; Z optionally substituted with one or more hydroxy, thiol, alkoxy, thioalkoxy, amino, halo, NR²³SO₂R²⁴, —CO, —CNOH, —CNOR²⁶, —CNNR²⁷, —CNNCOR²⁸ and —CNNSO₂R²⁹; and
R⁸, R⁹, R¹⁰, R¹¹, R¹², R¹³R¹⁴, R¹⁵, R¹⁶, R¹⁷, R¹⁸, R¹⁹, R²⁰, R²¹, R²², R²³, R²⁴, and R²⁶ are independently selected from the group consisting of H, alkyl, alkenyl, alkynyl, cycloalkyl, cycloalkylalkyl, hydroxy, alkoxy, aryl, and alkyl-R²⁵ wherein R²⁵ is alkenyl, hydroxy, thiol, alkoxy, thioalkoxy, amino, alkylamino, dialkylamino, aryl, cyano, halo, sulfoxy, sulfonyl, —NR²⁷COOR²⁸, —NR²⁹C(O)R³⁰, —NR³¹SO₂R³², SO₂NR³¹R³²—C(O)NR³³R³⁴, and
R²⁷, R²⁸, R²⁹, R³⁰, R³¹, R³², R³³ and R³⁴ are, independently, hydrogen, alkyl, or cycloalkyl.

2. The compound of claim 1 wherein
Y is O;
R¹, R², R⁴, R⁵, and R⁷ are each independently H or alkyl;
R³ is morpholinyl;
R⁶ is —NH-Z-aryl.

3. The compound of claim 1 wherein R⁶ is —NH-alkyl-aryl.

4. The compound of claim 1 wherein R⁵ is methyl.

5. The compound of claim 1 wherein A or B is NH.

6. The compound of claim 1 wherein A or B is C=O.

7. The compound of claim 1 where A is a direct bond and B is C=O.

8. A pharmaceutical composition comprising the compound of claim 1 in a pharmaceutically acceptable carrier.

* * * * *